US011542318B2

(12) United States Patent
Li et al.

(10) Patent No.: US 11,542,318 B2
(45) Date of Patent: Jan. 3, 2023

(54) USE OF CHEMOKINE RECEPTOR CXCR5

(71) Applicant: GUANGZHOU BIO-GENE TECHNOLOGY CO., LTD, Guangdong (CN)

(72) Inventors: Guangchao Li, Guangdong (CN); Min Luo, Guangdong (CN); Jintao Guo, Guangdong (CN); Wenjun Mo, Guangdong (CN); Wen Ding, Guangdong (CN)

(73) Assignee: GUANGZHOU BIO-GENE TECHNOLOGY CO., LTD., Guangzhou (CN)

( * ) Notice: Subject to any disclaimer, the term of this patent is extended or adjusted under 35 U.S.C. 154(b) by 268 days.

(21) Appl. No.: 16/646,439

(22) PCT Filed: Dec. 12, 2019

(86) PCT No.: PCT/CN2019/124916
§ 371 (c)(1),
(2) Date: Mar. 11, 2020

(87) PCT Pub. No.: WO2020/135083
PCT Pub. Date: Jul. 2, 2020

(65) Prior Publication Data
US 2021/0214418 A1 Jul. 15, 2021

(30) Foreign Application Priority Data
Dec. 29, 2018 (CN) .......................... 201811643734.6

(51) Int. Cl.
*C07K 14/00* (2006.01)
*C07K 14/715* (2006.01)
*A61P 35/00* (2006.01)
*A61K 38/00* (2006.01)

(52) U.S. Cl.
CPC .......... *C07K 14/7158* (2013.01); *A61P 35/00* (2018.01); *A61K 38/00* (2013.01); *C12N 2740/15043* (2013.01)

(58) Field of Classification Search
None
See application file for complete search history.

(56) References Cited

PUBLICATIONS

PCT International Patent Application Publication No. WO 16/025454 A2 (Anthrogeneis Corp. [US/US]) , published Feb. 18, 2016.
Chinese Patent Application No. CN 109666074, published on Apr. 23, 2019, (Guangzhou Bio Gene Tech Co LTD) (including English language translation of Abstract).
Craddock, J.A. et al., "Enhanced Tumor Trafficking of GD2 Chimeric Antigen Receptor T Cells by Expression of the Chemokine Receptor CCR2b", J Immunother, 2010, vol. 33, No. 8, pp. 780-788.
Tang, J., "The tumor immune effect of CXCR5+CD8+ T cells in diffuse large B-cell lymphoma", International Immunopharmacology, 2017, vol. 50, pp. i-82.
Zhang, H. et al., "New Strategies for the Treatment of Solid Tumors with CAR-T Cells", Int. J. Biol. Sci., 2016, vol. 12, pp. 718-729.
Zhu, D. et al., "The Role Of Chemokine Cxcl13 And Its Receptor Cxcr5 In Tumors", Chin J Clin Lab Sci, 2013, vol. 36, No. 2, pp. 129-131 (including English language translation of Abstract).
Wang, D. et al., "Practice Of Cart Immunotherapy From Hematological Diseases To Solid Tumors" p. 79 including English language translation of Abstract).
International Search Report issued by the International Searching Authority (ISA/O.E.P.M.) dated Mar. 16, 2020 in connection with International Application No. PCT/CN2019/124916.
PCT International Patent Application Publication No. WO 16/025454 A2 (Anthrogeneis Corp. [US/US]), published Feb. 18, 2016 (Exhibit 1).
Chinese Patent Application No. CN 109666074, published on Apr. 23, 2019, (Guangzhou Bio Gene Tech Co LTD) (including English language translation of Abstract) (Exhibit 2).
Craddock, J.A. et al., "Enhanced Tumor Trafficking of GD2 Chimeric Antigen Receptor T Cells by Expression of the Chemokine Receptor CCR2b", J Immunother, 2010, vol. 33, No. 8, pp. 780-788 (Exhibit 3).
Tang, J., "The tumor immune effect of CXCR5+CD8+ T cells in diffuse large B-cell lymphoma", International Immunopharmacology, 2017, vol. 50, pp. i-82 (Exhibit 4).
Zhang, H. et al., "New Strategies for the Treatment of Solid Tumors with CAR-T Cells", Int. J. Biol. Sci., 2016, vol. 12, pp. 718-729 (Exhibit 5).
Zhu, D. et al., "The Role of Chemokine Cxcl13 And Its Receptor Cxcr5 in Tumors", Chin J Clin Lab Sci, 2018, vol. 36, No. 2, pp. 129-131 (including English language translation of Abstract) (Exhibit 6).
Wang, D. et al., "Practice of Cart Immunotherapy From Hematological Diseases to Solid Tumors" p. 79 including English language translation of Abstract) (Exhibit7).
International Search Report issued by the International Searching Authority (ISA/O.E.P.M.) dated Mar. 16, 2020 in connection with International Application No. PCT/CN2019/124916 (Exhibit 8).

*Primary Examiner* — Jeanette M Lieb
(74) *Attorney, Agent, or Firm* — Gary J. Gershik

(57) ABSTRACT

The present disclosure provides use of chemokine receptor CXCR5, wherein CAR-T cells with enhanced chemotaxis are obtained by modifying chimeric antigen receptor T cells (CAR-T cells) utilizing the chemotactic signal between CXCR5 and its ligand CXCL13. The chemokine receptor CXCR5 can guide CAR-T cells to migrate to tumors. It has an excellent ability to enhance the chemotaxis of CAR-T cells, can specifically clear tumor cells, and effectively solve the problem of poor efficacy of the existing CAR-T therapy for solid tumors, thereby exhibiting broad application prospects and great market value.

13 Claims, 10 Drawing Sheets
Specification includes a Sequence Listing.

| | Extracellular domain | | | Intracellular domain | | | |
|---|---|---|---|---|---|---|---|
| CD19-CAR | anti-CD19 scFv | Hinge | TM | 4-1BB | CD3ζ | | |
| CD19-CXCR5 CAR | anti-CD19 scFv | Hinge | TM | 4-1BB | CD3ζ | 2A | CXCR5 |
| CD20-CAR | anti-CD20 scFv | Hinge | TM | 4-1BB | CD3ζ | | |
| CD20-CXCR5 CAR | anti-CD20 scFv | Hinge | TM | 4-1BB | CD3ζ | 2A | CXCR5 |
| BCMA-CAR | anti-BCMA scFv | Hinge | TM | 4-1BB | CD3ζ | | |
| BCMA-CXCR5 CAR | anti-BCMA scFv | Hinge | TM | 4-1BB | CD3ζ | 2A | CXCR5 |
| CLL1-CAR | anti-CLL1 scFv | Hinge | TM | 4-1BB | CD3ζ | | |
| CLL1-CXCR5 CAR | anti-CLL1 scFv | Hinge | TM | 4-1BB | CD3ζ | 2A | CXCR5 |
| EGFR-CAR | anti-EGFR scFv | Hinge | TM | 4-1BB | CD3ζ | | |
| EGFR-CXR5-CAR | anti-EGFR scFv | Hinge | TM | 4-1BB | CD3ζ | 2A | CXCR5 |
| B7H3-CAR | anti-B7H3 scFv | Hinge | TM | 4-1BB | CD3ζ | | |
| B7H3-CXCR5 CAR | anti-B7H3 scFv | Hinge | TM | 4-1BB | CD3ζ | 2A | CXCR5 |
| HER2-CAR | anti-EGFR scFv | Hinge | TM | 4-1BB | CD3ζ | | |
| HER2-CXR5-CAR | anti-EGFR scFv | Hinge | TM | 4-1BB | CD3ζ | 2A | CXCR5 |
| GD2-CAR | anti-EGFR scFv | Hinge | TM | 4-1BB | CD3ζ | | |
| GD2-CXR5-CAR | anti-EGFR scFv | Hinge | TM | 4-1BB | CD3ζ | 2A | CXCR5 |
| GPC3-CAR | anti-CD20 scFv | Hinge | TM | 4-1BB | CD3ζ | | |
| GPC3-CXCR5 CAR | anti-CD20 scFv | Hinge | TM | 4-1BB | CD3ζ | 2A | CXCR5 |
| MUC1-CAR | anti-MUC1 scFv | Hinge | TM | 4-1BB | CD3ζ | | |
| MUC1-CXR5-CAR | anti-MUC1 scFv | Hinge | TM | 4-1BB | CD3ζ | 2A | CXCR5 |
| PSMA-CAR | anti-PSMA scFv | Hinge | TM | 4-1BB | CD3ζ | | |
| PSMA-CXR5-CAR | anti-PMSA scFv | Hinge | TM | 4-1BB | CD3ζ | 2A | CXCR5 |

Figure 4B

SEQUENCE LISTING

```
<160> NUMBER OF SEQ ID NOS: 28

<210> SEQ ID NO 1
<211> LENGTH: 486
<212> TYPE: PRT
<213> ORGANISM: Artificial Sequence
<220> FEATURE:
<223> OTHER INFORMATION: the amino acid sequence of CD19-CAR

<400> SEQUENCE: 1

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Ser Glu
```

```
                    130                 135                 140
Val Lys Leu Gln Glu Ser Gly Pro Gly Leu Val Ala Pro Gln Ser
145                 150                 155                 160

Leu Ser Val Thr Cys Thr Val Ser Gly Val Ser Leu Pro Asp Tyr Gly
                    165                 170                 175

Val Ser Trp Ile Arg Gln Pro Pro Arg Lys Gly Leu Glu Trp Leu Gly
                180                 185                 190

Val Ile Trp Gly Ser Glu Thr Thr Tyr Tyr Asn Ser Ala Leu Lys Ser
                195                 200                 205

Arg Leu Thr Ile Ile Lys Asp Asn Ser Lys Ser Gln Val Phe Leu Lys
            210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
                260                 265                 270

Thr Pro Ala Pro Thr Ile Ala Ser Gln Pro Leu Ser Leu Arg Pro Glu
                275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
                340                 345                 350

Thr Thr Gln Glu Glu Asp Gly Cys Ser Cys Arg Phe Pro Glu Glu Glu
                355                 360                 365

Glu Gly Gly Cys Glu Leu Arg Val Lys Phe Ser Arg Ser Ala Asp Ala
            370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 2
<211> LENGTH: 882
<212> TYPE: PRT
<213> ORGANISM: Artificial Sequence
<220> FEATURE:
<223> OTHER INFORMATION: the amino acid sequence of CD19-CXCR5 CAR

<400> SEQUENCE: 2

Met Ala Leu Pro Val Thr Ala Leu Leu Leu Pro Leu Ala Leu Leu Leu
```

```
  1               5                   10                  15
His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
            50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
            85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
            115                 120                 125

Gly Gly Gly Gly Ser Gly Gly Gly Ser Gly Gly Gly Ser Glu
            130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
            165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
            195                 200                 205

Arg Leu Thr Ile Ile Lys Asp Asn Ser Lys Ser Gln Val Phe Leu Lys
            210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
            245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
            325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
            370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Gly Arg Asp
            405                 410                 415

Pro Glu Met Gly Gly Lys Pro Arg Arg Lys Asn Pro Gln Glu Gly Leu
            420                 425                 430
```

```
Tyr Asn Glu Leu Gln Lys Asp Lys Met Ala Glu Ala Tyr Ser Glu Ile
        435                 440                 445

Gly Met Lys Gly Glu Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg Gly Ser Ala Ser Arg Gly Glu Gly Arg Gly
                    485                 490                 495

Ser Leu Leu Thr Cys Gly Asp Val Glu Glu Asn Pro Gly Pro Met Asn
                500                 505                 510

Tyr Pro Leu Thr Leu Glu Met Asp Leu Glu Asn Leu Glu Asp Leu Phe
            515                 520                 525

Trp Glu Leu Asp Arg Leu Asp Asn Tyr Asn Asp Thr Ser Leu Val Glu
        530                 535                 540

Asn His Leu Cys Pro Ala Thr Glu Gly Pro Leu Met Ala Ser Phe Lys
545                 550                 555                 560

Ala Val Phe Val Pro Val Ala Tyr Ser Leu Ile Phe Leu Leu Gly Val
                565                 570                 575

Ile Gly Asn Val Leu Val Leu Val Ile Leu Glu Arg His Arg Gln Thr
                580                 585                 590

Arg Ser Ser Thr Glu Thr Phe Leu Phe His Leu Ala Val Ala Asp Leu
            595                 600                 605

Leu Leu Val Phe Ile Leu Pro Phe Ala Val Ala Glu Gly Ser Val Gly
        610                 615                 620

Trp Val Leu Gly Thr Phe Leu Cys Lys Thr Val Ile Ala Leu His Lys
625                 630                 635                 640

Val Asn Phe Tyr Cys Ser Ser Leu Leu Leu Ala Cys Ile Ala Val Asp
                645                 650                 655

Arg Tyr Leu Ala Ile Val His Ala Val His Ala Tyr Arg His Arg Arg
            660                 665                 670

Leu Leu Ser Ile His Ile Thr Cys Gly Thr Ile Trp Leu Val Gly Phe
        675                 680                 685

Leu Leu Ala Leu Pro Glu Ile Leu Phe Ala Lys Val Ser Gln Gly His
        690                 695                 700

His Asn Asn Ser Leu Pro Arg Cys Thr Phe Ser Gln Glu Asn Gln Ala
705                 710                 715                 720

Glu Thr His Ala Trp Phe Thr Ser Arg Phe Leu Tyr His Val Ala Gly
                725                 730                 735

Phe Leu Leu Pro Met Leu Val Met Gly Trp Cys Tyr Val Gly Val Val
            740                 745                 750

His Arg Leu Arg Gln Ala Gln Arg Arg Pro Gln Arg Gln Lys Ala Val
        755                 760                 765

Arg Val Ala Ile Leu Val Thr Ser Ile Phe Phe Leu Cys Trp Ser Pro
770                 775                 780

Tyr His Ile Val Ile Phe Leu Asp Thr Leu Ala Arg Leu Lys Ala Val
785                 790                 795                 800

Asp Asn Thr Cys Lys Leu Asn Gly Ser Leu Pro Val Ala Ile Thr Met
                805                 810                 815

Cys Glu Phe Leu Gly Leu Ala His Cys Cys Leu Asn Pro Met Leu Tyr
            820                 825                 830

Thr Phe Ala Gly Val Lys Phe Arg Ser Asp Leu Ser Arg Leu Leu Thr
        835                 840                 845
```

```
Lys Leu Gly Cys Thr Gly Pro Ala Ser Leu Cys Gln Leu Phe Pro Gly
    850                 855                 860
Trp Arg Arg Ser Ser Leu Ser Glu Ser Glu Asn Ala Thr Ser Leu Thr
865                 870                 875                 880
Thr Phe

<210> SEQ ID NO 3
<211> LENGTH: 486
<212> TYPE: PRT
<213> ORGANISM: Artificial Sequence
<220> FEATURE:
<223> OTHER INFORMATION: the amino acid sequence of CD20-CAR

<400> SEQUENCE: 3

Met Ala Leu Pro Val Thr Ala Leu Leu Leu Pro Leu Ala Leu Leu Leu
1               5                   10                  15
His Ala Ala Arg Pro Gln Ile Val Leu Ser Gln Ser Pro Ala Ile Leu
                20                  25                  30
Ser Ala Ser Pro Gly Glu Lys Val Thr Met Thr Cys Arg Ala Ser Ser
            35                  40                  45
Ser Val Ser Tyr Ile His Trp Phe Gln Gln Lys Pro Gly Ser Ser Pro
        50                  55                  60
Lys Pro Trp Ile Tyr Ala Thr Ser Asn Leu Ala Ser Gly Val Pro Val
65                  70                  75                  80
Arg Phe Ser Gly Ser Gly Ser Gly Thr Ser Tyr Ser Leu Thr Ile Ser
                85                  90                  95
Arg Val Glu Ala Glu Asp Ala Ala Thr Tyr Tyr Cys Gln Gln Trp Thr
            100                 105                 110
Ser Asn Pro Pro Thr Phe Gly Gly Gly Thr Lys Leu Glu Ile Lys Gly
        115                 120                 125
Gly Gly Gly Ser Gly Gly Gly Gly Ser Gly Gly Gly Gly Ser Gln Val
130                 135                 140
Gln Leu Gln Gln Pro Gly Ala Glu Leu Val Lys Pro Gly Ala Ser Val
145                 150                 155                 160
Lys Met Ser Cys Lys Ala Ser Gly Tyr Thr Phe Thr Ser Tyr Asn Met
                165                 170                 175
His Trp Val Lys Gln Thr Pro Gly Arg Gly Leu Glu Trp Ile Gly Ala
            180                 185                 190
Ile Tyr Pro Gly Asn Gly Asp Thr Ser Tyr Asn Gln Lys Phe Lys Gly
        195                 200                 205
Lys Ala Thr Leu Thr Ala Asp Lys Ser Ser Ser Thr Ala Tyr Met Gln
210                 215                 220
Leu Ser Ser Leu Thr Ser Glu Asp Ser Ala Val Tyr Tyr Cys Ala Arg
225                 230                 235                 240
Ser Thr Tyr Tyr Gly Gly Asp Trp Tyr Phe Asn Val Trp Gly Ala Gly
                245                 250                 255
Thr Thr Val Thr Val Ser Ala Thr Thr Thr Pro Ala Pro Arg Pro Pro
            260                 265                 270
Thr Pro Ala Pro Thr Ile Ala Ser Gln Pro Leu Ser Leu Arg Pro Glu
        275                 280                 285
Ala Cys Arg Pro Ala Ala Gly Gly Ala Val His Thr Arg Gly Leu Asp
290                 295                 300
Phe Ala Cys Asp Ile Tyr Ile Trp Ala Pro Leu Ala Gly Thr Cys Gly
305                 310                 315                 320
Val Leu Leu Leu Ser Leu Val Ile Thr Leu Tyr Cys Lys Arg Gly Arg
```

```
                    325                 330                 335
Lys Lys Leu Leu Tyr Ile Phe Lys Gln Pro Phe Met Arg Pro Val Gln
                340                 345                 350

Thr Thr Gln Glu Glu Asp Gly Cys Ser Cys Arg Phe Pro Glu Glu Glu
                355                 360                 365

Glu Gly Gly Cys Glu Leu Arg Val Lys Phe Ser Arg Ser Ala Asp Ala
            370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
                435                 440                 445

Gly Met Lys Gly Glu Arg Arg Arg Gly Lys Gly His Asp Gly Leu Tyr
            450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 4
<211> LENGTH: 882
<212> TYPE: PRT
<213> ORGANISM: Artificial Sequence
<220> FEATURE:
<223> OTHER INFORMATION: the amino acid sequence of CD20-CXCR5 CAR

<400> SEQUENCE: 4

Met Ala Leu Pro Val Thr Ala Leu Leu Leu Pro Leu Ala Leu Leu Leu
1               5                   10                  15

His Ala Ala Arg Pro Gln Ile Val Leu Ser Gln Ser Pro Ala Ile Leu
                20                  25                  30

Ser Ala Ser Pro Gly Glu Lys Val Thr Met Thr Cys Arg Ala Ser Ser
            35                  40                  45

Ser Val Ser Tyr Ile His Trp Phe Gln Gln Lys Pro Gly Ser Ser Pro
    50                  55                  60

Lys Pro Trp Ile Tyr Ala Thr Ser Asn Leu Ala Ser Gly Val Pro Val
65                  70                  75                  80

Arg Phe Ser Gly Ser Gly Ser Gly Thr Ser Tyr Ser Leu Thr Ile Ser
                85                  90                  95

Arg Val Glu Ala Glu Asp Ala Ala Thr Tyr Tyr Cys Gln Gln Trp Thr
                100                 105                 110

Ser Asn Pro Pro Thr Phe Gly Gly Gly Thr Lys Leu Glu Ile Lys Gly
            115                 120                 125

Gly Gly Gly Ser Gly Gly Gly Gly Ser Gly Gly Gly Gly Ser Gln Val
    130                 135                 140

Gln Leu Gln Gln Pro Gly Ala Glu Leu Val Lys Pro Gly Ala Ser Val
145                 150                 155                 160

Lys Met Ser Cys Lys Ala Ser Gly Tyr Thr Phe Thr Ser Tyr Asn Met
                165                 170                 175

His Trp Val Lys Gln Thr Pro Gly Arg Gly Leu Glu Trp Ile Gly Ala
                180                 185                 190

Ile Tyr Pro Gly Asn Gly Asp Thr Ser Tyr Asn Gln Lys Phe Lys Gly
```

```
                    195                 200                 205
Lys Ala Thr Leu Thr Ala Asp Lys Ser Ser Thr Ala Tyr Met Gln
210                 215                 220

Leu Ser Ser Leu Thr Ser Glu Asp Ser Ala Val Tyr Tyr Cys Ala Arg
225                 230                 235                 240

Ser Thr Tyr Tyr Gly Asp Trp Tyr Phe Asn Val Trp Gly Ala Gly
                245                 250                 255

Thr Thr Val Thr Val Ser Ala Thr Thr Thr Pro Ala Pro Arg Pro Pro
                260                 265                 270

Thr Pro Ala Pro Thr Ile Ala Ser Gln Pro Leu Ser Leu Arg Pro Glu
                275                 280                 285

Ala Cys Arg Pro Ala Ala Gly Gly Ala Val His Thr Arg Gly Leu Asp
                290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
                340                 345                 350

Thr Thr Gln Glu Glu Asp Gly Cys Ser Cys Arg Phe Pro Glu Glu Glu
                355                 360                 365

Glu Gly Gly Cys Glu Leu Arg Val Lys Phe Ser Arg Ser Ala Asp Ala
                370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
                435                 440                 445

Gly Met Lys Gly Glu Arg Arg Arg Gly Lys Gly His Asp Gly Leu Tyr
                450                 455                 460

Gln Gly Leu Ser Thr Ala Thr Lys Asp Thr Tyr Asp Ala Leu His Met
465                 470                 475                 480

Gln Ala Leu Pro Pro Arg Gly Ser Ala Ser Arg Gly Glu Gly Arg Gly
                485                 490                 495

Ser Leu Leu Thr Cys Gly Asp Val Glu Glu Asn Pro Gly Pro Met Asn
                500                 505                 510

Tyr Pro Leu Thr Leu Glu Met Asp Leu Glu Asn Leu Glu Asp Leu Phe
                515                 520                 525

Trp Glu Leu Asp Arg Leu Asp Asn Tyr Asn Asp Thr Ser Leu Val Glu
                530                 535                 540

Asn His Leu Cys Pro Ala Thr Glu Gly Pro Leu Met Ala Ser Phe Lys
545                 550                 555                 560

Ala Val Phe Val Pro Val Ala Tyr Ser Leu Ile Phe Leu Leu Gly Val
                565                 570                 575

Ile Gly Asn Val Leu Val Leu Val Ile Leu Glu Arg His Arg Gln Thr
                580                 585                 590

Arg Ser Ser Thr Glu Thr Phe Leu Phe His Leu Ala Val Ala Asp Leu
                595                 600                 605

Leu Leu Val Phe Ile Leu Pro Phe Ala Val Ala Glu Gly Ser Val Gly
                610                 615                 620
```

-continued

Trp Val Leu Gly Thr Phe Leu Cys Lys Thr Val Ile Ala Leu His Lys
625                 630                 635                 640

Val Asn Phe Tyr Cys Ser Ser Leu Leu Leu Ala Cys Ile Ala Val Asp
                645                 650                 655

Arg Tyr Leu Ala Ile Val His Ala Val His Ala Tyr Arg His Arg Arg
            660                 665                 670

Leu Leu Ser Ile His Ile Thr Cys Gly Thr Ile Trp Leu Val Gly Phe
        675                 680                 685

Leu Leu Ala Leu Pro Glu Ile Leu Phe Ala Lys Val Ser Gln Gly His
690                 695                 700

His Asn Asn Ser Leu Pro Arg Cys Thr Phe Ser Gln Glu Asn Gln Ala
705                 710                 715                 720

Glu Thr His Ala Trp Phe Thr Ser Arg Phe Leu Tyr His Val Ala Gly
                725                 730                 735

Phe Leu Leu Pro Met Leu Val Met Gly Trp Cys Tyr Val Gly Val Val
            740                 745                 750

His Arg Leu Arg Gln Ala Gln Arg Arg Pro Gln Arg Gln Lys Ala Val
        755                 760                 765

Arg Val Ala Ile Leu Val Thr Ser Ile Phe Phe Leu Cys Trp Ser Pro
770                 775                 780

Tyr His Ile Val Ile Phe Leu Asp Thr Leu Ala Arg Leu Lys Ala Val
785                 790                 795                 800

Asp Asn Thr Cys Lys Leu Asn Gly Ser Leu Pro Val Ala Ile Thr Met
                805                 810                 815

Cys Glu Phe Leu Gly Leu Ala His Cys Cys Leu Asn Pro Met Leu Tyr
            820                 825                 830

Thr Phe Ala Gly Val Lys Phe Arg Ser Asp Leu Ser Arg Leu Leu Thr
        835                 840                 845

Lys Leu Gly Cys Thr Gly Pro Ala Ser Leu Cys Gln Leu Phe Pro Gly
850                 855                 860

Trp Arg Arg Ser Ser Leu Ser Glu Ser Glu Asn Ala Thr Ser Leu Thr
865                 870                 875                 880

Thr Phe

<210> SEQ ID NO 5
<211> LENGTH: 489
<212> TYPE: PRT
<213> ORGANISM: Artificial Sequence
<220> FEATURE:
<223> OTHER INFORMATION: the amino acid sequence of BCMA-CAR

<400> SEQUENCE: 5

Met Ala Leu Pro Val Thr Ala Leu Leu Leu Pro Leu Ala Leu Leu Leu
1               5                   10                  15

His Ala Ala Arg Pro Ser Tyr Val Leu Thr Gln Pro Pro Ser Val Ser
                20                  25                  30

Val Ala Pro Gly Gln Thr Ala Arg Ile Thr Cys Gly Gly Asn Asn Ile
            35                  40                  45

Gly Ser Lys Ser Val His Trp Tyr Gln Gln Pro Pro Gly Gln Ala Pro
        50                  55                  60

Val Val Val Val Tyr Asp Asp Ser Asp Arg Pro Ser Gly Ile Pro Glu
65                  70                  75                  80

Arg Phe Ser Gly Ser Asn Ser Gly Asn Thr Ala Thr Leu Thr Ile Ser
                85                  90                  95

Arg Val Glu Ala Gly Asp Glu Ala Val Tyr Tyr Cys Gln Val Trp Asp
                100                 105                 110

Ser Ser Ser Asp His Val Val Phe Gly Gly Gly Thr Lys Leu Thr Val
            115                 120                 125

Leu Gly Gly Gly Gly Ser Gly Gly Gly Gly Ser Gly Gly Gly Gly Ser
130                 135                 140

Gln Leu Gln Leu Gln Glu Ser Gly Pro Gly Leu Val Lys Pro Ser Glu
145                 150                 155                 160

Thr Leu Ser Leu Thr Cys Thr Val Ser Gly Ser Ile Ser Ser Gly
                165                 170                 175

Ser Tyr Phe Trp Gly Trp Ile Arg Gln Pro Pro Gly Lys Gly Leu Glu
            180                 185                 190

Trp Ile Gly Ser Ile Tyr Tyr Ser Gly Ile Thr Tyr Tyr Asn Pro Ser
            195                 200                 205

Leu Lys Ser Arg Val Thr Ile Ser Val Asp Thr Ser Lys Asn Gln Phe
210                 215                 220

Ser Leu Lys Leu Ser Ser Val Thr Ala Ala Asp Thr Ala Val Tyr Tyr
225                 230                 235                 240

Cys Ala Arg His Asp Gly Ala Val Ala Gly Leu Phe Asp Tyr Trp Gly
                245                 250                 255

Gln Gly Thr Leu Val Thr Val Ser Ser Ala Thr Thr Pro Ala Pro
            260                 265                 270

Arg Pro Pro Thr Pro Ala Pro Thr Ile Ala Ser Gln Pro Leu Ser Leu
            275                 280                 285

Arg Pro Glu Ala Cys Arg Pro Ala Ala Gly Gly Ala Val His Thr Arg
290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
            355                 360                 365

Glu Glu Glu Glu Gly Gly Cys Glu Leu Arg Val Lys Phe Ser Arg Ser
            370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
            435                 440                 445

Ser Glu Ile Gly Met Lys Gly Glu Arg Arg Arg Gly Lys Gly His Asp
            450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 6
<211> LENGTH: 883
<212> TYPE: PRT

<213> ORGANISM: Artificial Sequence
<220> FEATURE:
<223> OTHER INFORMATION: the amino acid sequence of BCMA-CXCR5 CAR

<400> SEQUENCE: 6

```
Met Ala Leu Pro Val Thr Ala Leu Leu Leu Pro Leu Ala Leu Leu Leu
1               5                   10                  15

His Ala Ala Arg Pro Ser Tyr Val Leu Thr Gln Pro Pro Ser Val Ser
            20                  25                  30

Val Ala Pro Gly Gln Thr Ala Arg Ile Thr Cys Gly Asn Asn Ile
        35                  40                  45

Gly Ser Lys Ser Val His Trp Tyr Gln Gln Pro Pro Gly Gln Ala Pro
    50                  55                  60

Val Val Val Val Tyr Asp Asp Ser Asp Arg Pro Ser Gly Ile Pro Glu
65                  70                  75                  80

Arg Phe Ser Gly Ser Asn Ser Gly Asn Thr Ala Thr Leu Thr Ile Ser
                85                  90                  95

Arg Val Glu Ala Gly Asp Glu Ala Val Tyr Tyr Cys Gln Val Trp Asp
            100                 105                 110

Ser Ser Ser Asp His Val Val Phe Gly Gly Gly Thr Lys Leu Thr Val
        115                 120                 125

Leu Gly Gly Gly Gly Ser Gly Gly Gly Gly Ser Gly Gly Gly Gly Ser
    130                 135                 140

Gln Leu Gln Leu Gln Glu Ser Gly Pro Gly Leu Val Lys Pro Ser Glu
145                 150                 155                 160

Thr Leu Ser Leu Thr Cys Thr Val Ser Gly Gly Ser Ile Ser Ser Gly
                165                 170                 175

Ser Tyr Phe Trp Gly Trp Ile Arg Gln Pro Pro Gly Lys Gly Leu Glu
            180                 185                 190

Trp Ile Gly Ser Ile Tyr Tyr Ser Gly Ile Thr Tyr Tyr Asn Pro Ser
        195                 200                 205

Leu Lys Ser Arg Val Thr Ile Ser Val Asp Thr Ser Lys Asn Gln Phe
    210                 215                 220

Ser Leu Lys Leu Ser Ser Val Thr Ala Ala Asp Thr Ala Val Tyr Tyr
225                 230                 235                 240

Cys Ala Arg His Asp Gly Ala Val Ala Gly Leu Phe Asp Tyr Trp Gly
                245                 250                 255

Gln Gly Thr Leu Val Thr Val Ser Ser Ala Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
```

```
            385                 390                 395                 400
        Leu Asn Leu Gly Arg Arg Glu Glu Tyr Asp Val Leu Asp Lys Arg Arg
                        405                 410                 415

Gly Arg Asp Pro Glu Met Gly Gly Lys Pro Arg Arg Lys Asn Pro Gln
                        420                 425                 430

Glu Gly Leu Tyr Asn Glu Leu Gln Lys Asp Lys Met Ala Glu Ala Tyr
                        435                 440                 445

Ser Glu Ile Gly Met Lys Gly Glu Arg Arg Gly Lys Gly His Asp
            450                 455                 460

Gly Leu Tyr Gln Gly Leu Ser Thr Ala Thr Lys Asp Thr Tyr Asp Ala
        465                 470                 475                 480

Leu His Met Gln Ala Leu Pro Pro Arg Ala Ser Arg Gly Glu Gly Arg
                        485                 490                 495

Gly Ser Leu Leu Thr Cys Gly Asp Val Glu Glu Asn Pro Gly Pro Met
                        500                 505                 510

Asn Tyr Pro Leu Thr Leu Glu Met Asp Leu Glu Asn Leu Glu Asp Leu
                        515                 520                 525

Phe Trp Glu Leu Asp Arg Leu Asp Asn Tyr Asn Asp Thr Ser Leu Val
                        530                 535                 540

Glu Asn His Leu Cys Pro Ala Thr Glu Gly Pro Leu Met Ala Ser Phe
        545                 550                 555                 560

Lys Ala Val Phe Val Pro Val Ala Tyr Ser Leu Ile Phe Leu Leu Gly
                        565                 570                 575

Val Ile Gly Asn Val Leu Val Leu Val Ile Leu Glu Arg His Arg Gln
                        580                 585                 590

Thr Arg Ser Ser Thr Glu Thr Phe Leu Phe His Leu Ala Val Ala Asp
                        595                 600                 605

Leu Leu Leu Val Phe Ile Leu Pro Phe Ala Val Ala Glu Gly Ser Val
                        610                 615                 620

Gly Trp Val Leu Gly Thr Phe Leu Cys Lys Thr Val Ile Ala Leu His
        625                 630                 635                 640

Lys Val Asn Phe Tyr Cys Ser Ser Leu Leu Leu Ala Cys Ile Ala Val
                        645                 650                 655

Asp Arg Tyr Leu Ala Ile Val His Ala Val His Ala Tyr Arg His Arg
                        660                 665                 670

Arg Leu Leu Ser Ile His Ile Thr Cys Gly Thr Ile Trp Leu Val Gly
                        675                 680                 685

Phe Leu Leu Ala Leu Pro Glu Ile Leu Phe Ala Lys Val Ser Gln Gly
                        690                 695                 700

His His Asn Asn Ser Leu Pro Arg Cys Thr Phe Ser Gln Glu Asn Gln
        705                 710                 715                 720

Ala Glu Thr His Ala Trp Phe Thr Ser Arg Phe Leu Tyr His Val Ala
                        725                 730                 735

Gly Phe Leu Leu Pro Met Leu Val Met Gly Trp Cys Tyr Val Gly Val
                        740                 745                 750

Val His Arg Leu Arg Gln Ala Gln Arg Arg Pro Gln Arg Gln Lys Ala
                        755                 760                 765

Val Arg Val Ala Ile Leu Val Thr Ser Ile Phe Phe Leu Cys Trp Ser
                        770                 775                 780

Pro Tyr His Ile Val Ile Phe Leu Asp Thr Leu Ala Arg Leu Lys Ala
        785                 790                 795                 800

Val Asp Asn Thr Cys Lys Leu Asn Gly Ser Leu Pro Val Ala Ile Thr
                        805                 810                 815
```

Met Cys Glu Phe Leu Gly Leu Ala His Cys Cys Leu Asn Pro Met Leu
            820                 825                 830

Tyr Thr Phe Ala Gly Val Lys Phe Arg Ser Asp Leu Ser Arg Leu Leu
            835                 840                 845

Thr Lys Leu Gly Cys Thr Gly Pro Ala Ser Leu Cys Gln Leu Phe Pro
850                 855                 860

Gly Trp Arg Arg Ser Ser Leu Ser Glu Ser Glu Asn Ala Thr Ser Leu
865                 870                 875                 880

Thr Thr Phe

<210> SEQ ID NO 7
<211> LENGTH: 489
<212> TYPE: PRT
<213> ORGANISM: Artificial Sequence
<220> FEATURE:
<223> OTHER INFORMATION: the amino acid sequence of CLL1-CAR

<400> SEQUENCE: 7

Met Ala Leu Pro Val Thr Ala Leu Leu Leu Pro Leu Ala Leu Leu Leu
1               5                   10                  15

His Ala Ala Arg Pro Glu Asn Val Leu Thr Gln Ser Pro Ala Ile Met
            20                  25                  30

Ser Ala Ser Pro Gly Glu Lys Val Thr Met Thr Cys Arg Ala Ser Ser
        35                  40                  45

Asn Val Ile Ser Ser Tyr Val His Trp Tyr Gln Gln Arg Ser Gly Ala
    50                  55                  60

Ser Pro Lys Leu Trp Ile Tyr Ser Thr Ser Asn Leu Ala Ser Gly Val
65                  70                  75                  80

Pro Ala Arg Phe Ser Gly Ser Gly Ser Gly Thr Ser Tyr Ser Leu Thr
                85                  90                  95

Ile Ser Ser Val Glu Ala Glu Asp Ala Ala Thr Tyr Tyr Cys Gln Gln
            100                 105                 110

Tyr Ser Gly Tyr Pro Leu Thr Phe Gly Ala Gly Thr Lys Leu Glu Leu
        115                 120                 125

Gly Gly Gly Gly Ser Gly Gly Gly Gly Ser Gly Gly Gly Gly Ser Asp
    130                 135                 140

Ile Gln Leu Gln Glu Ser Gly Pro Gly Leu Val Lys Pro Ser Gln Ser
145                 150                 155                 160

Leu Ser Leu Thr Cys Ser Val Thr Gly Tyr Ser Ile Thr Ser Ala Tyr
                165                 170                 175

Tyr Trp Asn Trp Ile Arg Gln Phe Pro Gly Asn Lys Leu Glu Trp Met
            180                 185                 190

Gly Tyr Ile Ser Tyr Asp Gly Arg Asn Asn Tyr Asn Pro Ser Leu Lys
        195                 200                 205

Asn Arg Ile Ser Ile Thr Arg Asp Thr Ser Lys Asn Gln Phe Phe Leu
    210                 215                 220

Lys Leu Asn Ser Val Thr Thr Glu Asp Thr Ala Thr Tyr Tyr Cys Ala
225                 230                 235                 240

Lys Glu Gly Asp Tyr Asp Val Gly Asn Tyr Tyr Ala Met Asp Tyr Trp
                245                 250                 255

Gly Gln Gly Thr Ser Val Thr Val Ser Ser Thr Thr Pro Ala Pro
            260                 265                 270

Arg Pro Pro Thr Pro Ala Pro Thr Ile Ala Ser Gln Pro Leu Ser Leu
        275                 280                 285

```
Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
                340                 345                 350

Pro Val Gln Thr Thr Gln Glu Asp Gly Cys Ser Cys Arg Phe Pro
                355                 360                 365

Glu Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
                420                 425                 430

Glu Gly Leu Tyr Asn Glu Leu Gln Lys Asp Lys Met Ala Glu Ala Tyr
                435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 8
<211> LENGTH: 883
<212> TYPE: PRT
<213> ORGANISM: Artificial Sequence
<220> FEATURE:
<223> OTHER INFORMATION: the amino acid sequence of CLL1-CXCR5 CAR

<400> SEQUENCE: 8

Met Ala Leu Pro Val Thr Ala Leu Leu Leu Pro Leu Ala Leu Leu Leu
1               5                  10                  15

His Ala Ala Arg Pro Glu Asn Val Leu Thr Gln Ser Pro Ala Ile Met
                20                  25                  30

Ser Ala Ser Pro Gly Glu Lys Val Thr Met Thr Cys Arg Ala Ser Ser
            35                  40                  45

Asn Val Ile Ser Ser Tyr Val His Trp Tyr Gln Gln Arg Ser Gly Ala
    50                  55                  60

Ser Pro Lys Leu Trp Ile Tyr Ser Thr Ser Asn Leu Ala Ser Gly Val
65                  70                  75                  80

Pro Ala Arg Phe Ser Gly Ser Gly Ser Gly Thr Ser Tyr Ser Leu Thr
                85                  90                  95

Ile Ser Ser Val Glu Ala Glu Asp Ala Ala Thr Tyr Tyr Cys Gln Gln
                100                 105                 110

Tyr Ser Gly Tyr Pro Leu Thr Phe Gly Ala Gly Thr Lys Leu Glu Leu
            115                 120                 125

Gly Gly Gly Gly Ser Gly Gly Gly Gly Ser Gly Gly Gly Gly Ser Asp
    130                 135                 140

Ile Gln Leu Gln Glu Ser Gly Pro Gly Leu Val Lys Pro Ser Gln Ser
145                 150                 155                 160
```

-continued

```
Leu Ser Leu Thr Cys Ser Val Thr Gly Tyr Ser Ile Thr Ser Ala Tyr
            165                 170                 175

Tyr Trp Asn Trp Ile Arg Gln Phe Pro Gly Asn Lys Leu Glu Trp Met
        180                 185                 190

Gly Tyr Ile Ser Tyr Asp Gly Arg Asn Asn Tyr Asn Pro Ser Leu Lys
            195                 200                 205

Asn Arg Ile Ser Ile Thr Arg Asp Thr Ser Lys Asn Gln Phe Phe Leu
        210                 215                 220

Lys Leu Asn Ser Val Thr Thr Glu Asp Thr Ala Thr Tyr Tyr Cys Ala
225                 230                 235                 240

Lys Glu Gly Asp Tyr Asp Val Gly Asn Tyr Tyr Ala Met Asp Tyr Trp
                245                 250                 255

Gly Gln Gly Thr Ser Val Thr Val Ser Ser Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
        290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
                340                 345                 350

Pro Val Gln Thr Thr Gln Glu Glu Asp Gly Cys Ser Cys Arg Phe Pro
            355                 360                 365

Glu Glu Glu Glu Gly Gly Cys Glu Leu Arg Val Lys Phe Ser Arg Ser
        370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg Ala Ser Arg Gly Glu Gly Arg
            485                 490                 495

Gly Ser Leu Leu Thr Cys Gly Asp Val Glu Glu Asn Pro Gly Pro Met
        500                 505                 510

Asn Tyr Pro Leu Thr Leu Glu Met Asp Leu Glu Asn Leu Glu Asp Leu
            515                 520                 525

Phe Trp Glu Leu Asp Arg Leu Asp Asn Tyr Asn Asp Thr Ser Leu Val
        530                 535                 540

Glu Asn His Leu Cys Pro Ala Thr Glu Gly Pro Leu Met Ala Ser Phe
545                 550                 555                 560

Lys Ala Val Phe Val Pro Val Ala Tyr Ser Leu Ile Phe Leu Leu Gly
                565                 570                 575

Val Ile Gly Asn Val Leu Val Leu Val Ile Leu Glu Arg His Arg Gln
```

```
                580             585             590
Thr Arg Ser Ser Thr Glu Thr Phe Leu Phe His Leu Ala Val Ala Asp
            595             600             605
Leu Leu Leu Val Phe Ile Leu Pro Phe Ala Val Ala Glu Gly Ser Val
        610             615             620
Gly Trp Val Leu Gly Thr Phe Leu Cys Lys Thr Val Ile Ala Leu His
625             630             635             640
Lys Val Asn Phe Tyr Cys Ser Ser Leu Leu Ala Cys Ile Ala Val
            645             650             655
Asp Arg Tyr Leu Ala Ile Val His Ala Val His Ala Tyr Arg His Arg
            660             665             670
Arg Leu Leu Ser Ile His Ile Thr Cys Gly Thr Ile Trp Leu Val Gly
            675             680             685
Phe Leu Leu Ala Leu Pro Glu Ile Leu Phe Ala Lys Val Ser Gln Gly
            690             695             700
His His Asn Asn Ser Leu Pro Arg Cys Thr Phe Ser Gln Glu Asn Gln
705             710             715             720
Ala Glu Thr His Ala Trp Phe Thr Ser Arg Phe Leu Tyr His Val Ala
            725             730             735
Gly Phe Leu Leu Pro Met Leu Val Met Gly Trp Cys Tyr Val Gly Val
            740             745             750
Val His Arg Leu Arg Gln Ala Gln Arg Arg Pro Gln Arg Gln Lys Ala
            755             760             765
Val Arg Val Ala Ile Leu Val Thr Ser Ile Phe Phe Leu Cys Trp Ser
            770             775             780
Pro Tyr His Ile Val Ile Phe Leu Asp Thr Leu Ala Arg Leu Lys Ala
785             790             795             800
Val Asp Asn Thr Cys Lys Leu Asn Gly Ser Leu Pro Val Ala Ile Thr
            805             810             815
Met Cys Glu Phe Leu Gly Leu Ala His Cys Cys Leu Asn Pro Met Leu
            820             825             830
Tyr Thr Phe Ala Gly Val Lys Phe Arg Ser Asp Leu Ser Arg Leu Leu
            835             840             845
Thr Lys Leu Gly Cys Thr Gly Pro Ala Ser Leu Cys Gln Leu Phe Pro
        850             855             860
Gly Trp Arg Arg Ser Ser Leu Ser Glu Ser Glu Asn Ala Thr Ser Leu
865             870             875             880
Thr Thr Phe

<210> SEQ ID NO 9
<211> LENGTH: 485
<212> TYPE: PRT
<213> ORGANISM: Artificial Sequence
<220> FEATURE:
<223> OTHER INFORMATION: the amino acid sequence of EGFR-CAR

<400> SEQUENCE: 9

Met Ala Leu Pro Val Thr Ala Leu Leu Leu Pro Leu Ala Leu Leu Leu
1               5                   10                  15
His Ala Ala Arg Pro Asp Ile Leu Leu Thr Gln Ser Pro Val Ile Leu
            20                  25                  30
Ser Val Ser Pro Gly Glu Arg Val Ser Phe Ser Cys Arg Ala Ser Gln
        35                  40                  45
Ser Ile Gly Thr Asn Ile His Trp Tyr Gln Gln Arg Thr Asn Gly Ser
    50                  55                  60
```

```
Pro Arg Leu Leu Ile Lys Tyr Ala Ser Glu Ser Ile Ser Gly Ile Pro
 65                  70                  75                  80

Ser Arg Phe Ser Gly Ser Gly Ser Gly Thr Asp Phe Thr Leu Ser Ile
             85                  90                  95

Asn Ser Val Glu Ser Glu Asp Ile Ala Asp Tyr Tyr Cys Gln Gln Asn
            100                 105                 110

Asn Asn Trp Pro Thr Thr Phe Gly Ala Gly Thr Lys Leu Glu Leu Lys
            115                 120                 125

Gly Gly Gly Gly Ser Gly Gly Gly Ser Gly Gly Gly Gly Ser Gln
        130                 135                 140

Val Gln Leu Lys Gln Ser Gly Pro Gly Leu Val Gln Pro Ser Gln Ser
145                 150                 155                 160

Leu Ser Ile Thr Cys Thr Val Ser Gly Phe Ser Leu Thr Asn Tyr Gly
                165                 170                 175

Val His Trp Val Arg Gln Ser Pro Gly Lys Gly Leu Glu Trp Leu Gly
            180                 185                 190

Val Ile Trp Ser Gly Gly Asn Thr Asp Tyr Asn Thr Pro Phe Thr Ser
            195                 200                 205

Arg Leu Ser Ile Asn Lys Asp Asn Ser Lys Ser Gln Val Phe Phe Lys
210                 215                 220

Met Asn Ser Leu Gln Ser Gln Asp Thr Ala Ile Tyr Tyr Cys Ala Arg
225                 230                 235                 240

Ala Leu Thr Tyr Tyr Asp Tyr Glu Phe Ala Tyr Trp Gly Gln Gly Thr
                245                 250                 255

Leu Val Thr Val Ser Ala Thr Thr Thr Pro Ala Pro Arg Pro Pro Thr
            260                 265                 270

Pro Ala Pro Thr Ile Ala Ser Gln Pro Leu Ser Leu Arg Pro Glu Ala
            275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
            355                 360                 365

Gly Gly Cys Glu Leu Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
            435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480
```

Ala Leu Pro Pro Arg
            485

<210> SEQ ID NO 10
<211> LENGTH: 879
<212> TYPE: PRT
<213> ORGANISM: Artificial Sequence
<220> FEATURE:
<223> OTHER INFORMATION: the amino acid sequence of EGFR-CXCR5 CAR

<400> SEQUENCE: 10

Met Ala Leu Pro Val Thr Ala Leu Leu Leu Pro Leu Ala Leu Leu Leu
1               5                   10                  15

His Ala Ala Arg Pro Asp Ile Leu Leu Thr Gln Ser Pro Val Ile Leu
            20                  25                  30

Ser Val Ser Pro Gly Glu Arg Val Ser Phe Ser Cys Arg Ala Ser Gln
        35                  40                  45

Ser Ile Gly Thr Asn Ile His Trp Tyr Gln Gln Arg Thr Asn Gly Ser
    50                  55                  60

Pro Arg Leu Leu Ile Lys Tyr Ala Ser Glu Ser Ile Ser Gly Ile Pro
65                  70                  75                  80

Ser Arg Phe Ser Gly Ser Gly Ser Gly Thr Asp Phe Thr Leu Ser Ile
                85                  90                  95

Asn Ser Val Glu Ser Glu Asp Ile Ala Asp Tyr Tyr Cys Gln Gln Asn
            100                 105                 110

Asn Asn Trp Pro Thr Thr Phe Gly Ala Gly Thr Lys Leu Glu Leu Lys
        115                 120                 125

Gly Gly Gly Gly Ser Gly Gly Gly Ser Gly Gly Gly Gly Ser Gln
    130                 135                 140

Val Gln Leu Lys Gln Ser Gly Pro Gly Leu Val Gln Pro Ser Gln Ser
145                 150                 155                 160

Leu Ser Ile Thr Cys Thr Val Ser Gly Phe Ser Leu Thr Asn Tyr Gly
                165                 170                 175

Val His Trp Val Arg Gln Ser Pro Gly Lys Gly Leu Glu Trp Leu Gly
            180                 185                 190

Val Ile Trp Ser Gly Gly Asn Thr Asp Tyr Asn Thr Pro Phe Thr Ser
        195                 200                 205

Arg Leu Ser Ile Asn Lys Asp Asn Ser Lys Ser Gln Val Phe Phe Lys
    210                 215                 220

Met Asn Ser Leu Gln Ser Gln Asp Thr Ala Ile Tyr Tyr Cys Ala Arg
225                 230                 235                 240

Ala Leu Thr Tyr Tyr Asp Tyr Glu Phe Ala Tyr Trp Gly Gln Gly Thr
                245                 250                 255

Leu Val Thr Val Ser Ala Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

```
Thr Gln Glu Glu Asp Gly Cys Ser Cys Arg Phe Pro Glu Glu Glu
        355                 360                 365

Gly Gly Cys Glu Leu Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg Ala Ser Arg Gly Glu Gly Arg Gly Ser Leu Leu
                485                 490                 495

Thr Cys Gly Asp Val Glu Glu Asn Pro Gly Pro Met Asn Tyr Pro Leu
            500                 505                 510

Thr Leu Glu Met Asp Leu Glu Asn Leu Glu Asp Leu Phe Trp Glu Leu
        515                 520                 525

Asp Arg Leu Asp Asn Tyr Asn Asp Thr Ser Leu Val Glu Asn His Leu
    530                 535                 540

Cys Pro Ala Thr Glu Gly Pro Leu Met Ala Ser Phe Lys Ala Val Phe
545                 550                 555                 560

Val Pro Val Ala Tyr Ser Leu Ile Phe Leu Leu Gly Val Ile Gly Asn
                565                 570                 575

Val Leu Val Leu Val Ile Leu Glu Arg His Arg Gln Thr Arg Ser Ser
            580                 585                 590

Thr Glu Thr Phe Leu Phe His Leu Ala Val Ala Asp Leu Leu Leu Val
        595                 600                 605

Phe Ile Leu Pro Phe Ala Val Ala Glu Gly Ser Val Gly Trp Val Leu
    610                 615                 620

Gly Thr Phe Leu Cys Lys Thr Val Ile Ala Leu His Lys Val Asn Phe
625                 630                 635                 640

Tyr Cys Ser Ser Leu Leu Leu Ala Cys Ile Ala Val Asp Arg Tyr Leu
                645                 650                 655

Ala Ile Val His Ala Val His Ala Tyr Arg His Arg Arg Leu Leu Ser
            660                 665                 670

Ile His Ile Thr Cys Gly Thr Ile Trp Leu Val Gly Phe Leu Leu Ala
        675                 680                 685

Leu Pro Glu Ile Leu Phe Ala Lys Val Ser Gln Gly His His Asn Asn
    690                 695                 700

Ser Leu Pro Arg Cys Thr Phe Ser Gln Glu Asn Gln Ala Glu Thr His
705                 710                 715                 720

Ala Trp Phe Thr Ser Arg Phe Leu Tyr His Val Ala Gly Phe Leu Leu
                725                 730                 735

Pro Met Leu Val Met Gly Trp Cys Tyr Val Gly Val Val His Arg Leu
            740                 745                 750

Arg Gln Ala Gln Arg Arg Pro Gln Arg Gln Lys Ala Val Arg Val Ala
        755                 760                 765

Ile Leu Val Thr Ser Ile Phe Phe Leu Cys Trp Ser Pro Tyr His Ile
```

```
            770                 775                 780
Val Ile Phe Leu Asp Thr Leu Ala Arg Leu Lys Ala Val Asp Asn Thr
785                 790                 795                 800

Cys Lys Leu Asn Gly Ser Leu Pro Val Ala Ile Thr Met Cys Glu Phe
                805                 810                 815

Leu Gly Leu Ala His Cys Cys Leu Asn Pro Met Leu Tyr Thr Phe Ala
            820                 825                 830

Gly Val Lys Phe Arg Ser Asp Leu Ser Arg Leu Leu Thr Lys Leu Gly
        835                 840                 845

Cys Thr Gly Pro Ala Ser Leu Cys Gln Leu Phe Pro Gly Trp Arg Arg
850                 855                 860

Ser Ser Leu Ser Glu Ser Glu Asn Ala Thr Ser Leu Thr Thr Phe
865                 870                 875

<210> SEQ ID NO 11
<211> LENGTH: 488
<212> TYPE: PRT
<213> ORGANISM: Artificial Sequence
<220> FEATURE:
<223> OTHER INFORMATION: the amino acid sequence of B7H3-CAR

<400> SEQUENCE: 11

Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Phe Leu
            20                  25                  30

Ser Ala Ser Val Gly Asp Arg Val Thr Ile Thr Cys Lys Ala Ser Gln
        35                  40                  45

Asn Val Asp Thr Asn Val Ala Trp Tyr Gln Gln Lys Pro Gly Lys Ala
    50                  55                  60

Pro Lys Ala Leu Ile Tyr Ser Ala Ser Tyr Arg Tyr Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Tyr
            100                 105                 110

Asn Asn Tyr Pro Phe Thr Phe Gly Gln Gly Thr Lys Leu Glu Ile Lys
        115                 120                 125

Gly Gly Gly Gly Ser Gly Gly Gly Gly Ser Gly Gly Gly Gly Ser Glu
    130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Phe Thr Phe Ser Ser Phe Gly
                165                 170                 175

Met His Trp Val Arg Gln Ala Pro Gly Lys Gly Leu Glu Trp Val Ala
            180                 185                 190

Tyr Ile Ser Ser Asp Ser Ser Ala Ile Tyr Tyr Ala Asp Thr Val Lys
        195                 200                 205

Gly Arg Phe Thr Ile Ser Arg Asp Asn Ala Lys Asn Ser Leu Tyr Leu
    210                 215                 220

Gln Met Asn Ser Leu Arg Asp Glu Asp Thr Ala Val Tyr Tyr Cys Gly
225                 230                 235                 240

Arg Gly Arg Glu Asn Ile Tyr Tyr Gly Ser Arg Leu Asp Tyr Trp Gly
                245                 250                 255

Gln Gly Thr Thr Val Thr Val Ser Ser Thr Thr Thr Pro Ala Pro Arg
```

```
                        260                 265                 270
Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
            290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
            370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
            450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485
```

<210> SEQ ID NO 12
<211> LENGTH: 882
<212> TYPE: PRT
<213> ORGANISM: Artificial Sequence
<220> FEATURE:
<223> OTHER INFORMATION: the amino acid sequence of B7H3-CXCR5 CAR

<400> SEQUENCE: 12

```
Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Phe Leu
                20                  25                  30

Ser Ala Ser Val Gly Asp Arg Val Thr Ile Thr Cys Lys Ala Ser Gln
            35                  40                  45

Asn Val Asp Thr Asn Val Ala Trp Tyr Gln Gln Lys Pro Gly Lys Ala
        50                  55                  60

Pro Lys Ala Leu Ile Tyr Ser Ala Ser Tyr Arg Tyr Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Tyr
            100                 105                 110

Asn Asn Tyr Pro Phe Thr Phe Gly Gln Gly Thr Lys Leu Glu Ile Lys
        115                 120                 125

Gly Gly Gly Gly Ser Gly Gly Gly Gly Ser Gly Gly Gly Gly Ser Glu
```

```
            130                 135                 140
Val Gln Leu Val Glu Ser Gly Gly Leu Val Gln Pro Gly Gly Ser
145                 150                 155                 160

Leu Arg Leu Ser Cys Ala Ala Ser Gly Phe Thr Phe Ser Ser Phe Gly
            165                 170                 175

Met His Trp Val Arg Gln Ala Pro Gly Lys Gly Leu Glu Trp Val Ala
            180                 185                 190

Tyr Ile Ser Ser Asp Ser Ser Ala Ile Tyr Tyr Ala Asp Thr Val Lys
            195                 200                 205

Gly Arg Phe Thr Ile Ser Arg Asp Asn Ala Lys Asn Ser Leu Tyr Leu
            210                 215                 220

Gln Met Asn Ser Leu Arg Asp Glu Asp Thr Ala Val Tyr Tyr Cys Gly
225                 230                 235                 240

Arg Gly Arg Glu Asn Ile Tyr Tyr Gly Ser Arg Leu Asp Tyr Trp Gly
            245                 250                 255

Gln Gly Thr Thr Val Thr Val Ser Ser Thr Thr Thr Pro Ala Pro Arg
            260                 265                 270

Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
            290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
            325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
            370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
            405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
            450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg Ala Ser Arg Gly Glu Gly Arg Gly
            485                 490                 495

Ser Leu Leu Thr Cys Gly Asp Val Glu Glu Asn Pro Gly Pro Met Asn
            500                 505                 510

Tyr Pro Leu Thr Leu Glu Met Asp Leu Glu Asn Leu Glu Asp Leu Phe
            515                 520                 525

Trp Glu Leu Asp Arg Leu Asp Asn Tyr Asn Asp Thr Ser Leu Val Glu
            530                 535                 540

Asn His Leu Cys Pro Ala Thr Glu Gly Pro Leu Met Ala Ser Phe Lys
545                 550                 555                 560
```

```
Ala Val Phe Val Pro Val Ala Tyr Ser Leu Ile Phe Leu Leu Gly Val
                565                 570                 575

Ile Gly Asn Val Leu Val Leu Val Ile Leu Glu Arg His Arg Gln Thr
            580                 585                 590

Arg Ser Ser Thr Glu Thr Phe Leu Phe His Leu Ala Val Ala Asp Leu
        595                 600                 605

Leu Leu Val Phe Ile Leu Pro Phe Ala Val Ala Glu Gly Ser Val Gly
    610                 615                 620

Trp Val Leu Gly Thr Phe Leu Cys Lys Thr Val Ile Ala Leu His Lys
625                 630                 635                 640

Val Asn Phe Tyr Cys Ser Ser Leu Leu Ala Cys Ile Ala Val Asp
                645                 650                 655

Arg Tyr Leu Ala Ile Val His Ala Val His Ala Tyr Arg His Arg Arg
                660                 665                 670

Leu Leu Ser Ile His Ile Thr Cys Gly Thr Ile Trp Leu Val Gly Phe
            675                 680                 685

Leu Leu Ala Leu Pro Glu Ile Leu Phe Ala Lys Val Ser Gln Gly His
        690                 695                 700

His Asn Asn Ser Leu Pro Arg Cys Thr Phe Ser Gln Glu Asn Gln Ala
705                 710                 715                 720

Glu Thr His Ala Trp Phe Thr Ser Arg Phe Leu Tyr His Val Ala Gly
                725                 730                 735

Phe Leu Leu Pro Met Leu Val Met Gly Trp Cys Tyr Val Gly Val Val
                740                 745                 750

His Arg Leu Arg Gln Ala Gln Arg Arg Pro Gln Arg Lys Ala Val
            755                 760                 765

Arg Val Ala Ile Leu Val Thr Ser Ile Phe Phe Leu Cys Trp Ser Pro
            770                 775                 780

Tyr His Ile Val Ile Phe Leu Asp Thr Leu Ala Arg Leu Lys Ala Val
785                 790                 795                 800

Asp Asn Thr Cys Lys Leu Asn Gly Ser Leu Pro Val Ala Ile Thr Met
                805                 810                 815

Cys Glu Phe Leu Gly Leu Ala His Cys Cys Leu Asn Pro Met Leu Tyr
                820                 825                 830

Thr Phe Ala Gly Val Lys Phe Arg Ser Asp Leu Ser Arg Leu Leu Thr
            835                 840                 845

Lys Leu Gly Cys Thr Gly Pro Ala Ser Leu Cys Gln Leu Phe Pro Gly
            850                 855                 860

Trp Arg Arg Ser Ser Leu Ser Glu Ser Glu Asn Ala Thr Ser Leu Thr
865                 870                 875                 880

Thr Phe

<210> SEQ ID NO 13
<211> LENGTH: 486
<212> TYPE: PRT
<213> ORGANISM: Artificial Sequence
<220> FEATURE:
<223> OTHER INFORMATION: the amino acid sequence of HER2-CAR

<400> SEQUENCE: 13

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30
```

-continued

```
Ser Ala Ser Val Gly Asp Arg Val Thr Ile Thr Cys Arg Ala Ser Gln
         35                  40                  45

Asp Val Asn Thr Ala Val Ala Trp Tyr Gln Gln Lys Pro Gly Lys Ala
     50                  55                  60

Pro Lys Leu Leu Ile Tyr Ser Ala Ser Phe Leu Tyr Ser Gly Val Pro
 65                  70                  75                  80

Ser Arg Phe Ser Gly Ser Arg Ser Gly Thr Asp Phe Thr Leu Thr Ile
                 85                  90                  95

Ser Ser Leu Gln Pro Glu Asp Phe Ala Thr Tyr Tyr Cys Gln Gln His
             100                 105                 110

Tyr Thr Thr Pro Pro Thr Phe Gly Gln Gly Thr Lys Val Glu Ile Lys
         115                 120                 125

Gly Gly Gly Gly Ser Gly Gly Gly Gly Ser Gly Gly Gly Gly Ser Glu
     130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Phe Asn Ile Lys Asp Thr Tyr
                 165                 170                 175

Ile His Trp Val Arg Gln Ala Pro Gly Lys Gly Leu Glu Trp Val Ala
             180                 185                 190

Arg Ile Tyr Pro Thr Asn Gly Tyr Thr Arg Tyr Ala Asp Ser Val Lys
         195                 200                 205

Gly Arg Phe Thr Ile Ser Ala Asp Thr Ser Lys Asn Thr Ala Tyr Leu
     210                 215                 220

Gln Met Asn Ser Leu Arg Ala Glu Asp Thr Ala Val Tyr Tyr Cys Ser
225                 230                 235                 240

Arg Trp Gly Gly Asp Gly Phe Tyr Ala Met Asp Tyr Trp Gly Gln Gly
                 245                 250                 255

Thr Leu Val Thr Val Ser Ser Thr Thr Thr Pro Ala Pro Arg Pro Pro
             260                 265                 270

Thr Pro Ala Pro Thr Ile Ala Ser Gln Pro Leu Ser Leu Arg Pro Glu
         275                 280                 285

Ala Cys Arg Pro Ala Ala Gly Gly Ala Val His Thr Arg Gly Leu Asp
     290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                 325                 330                 335

Lys Lys Leu Leu Tyr Ile Phe Lys Gln Pro Phe Met Arg Pro Val Gln
             340                 345                 350

Thr Thr Gln Glu Glu Asp Gly Cys Ser Cys Arg Phe Pro Glu Glu Glu
         355                 360                 365

Glu Gly Gly Cys Glu Leu Arg Val Lys Phe Ser Arg Ser Ala Asp Ala
     370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                 405                 410                 415

Pro Glu Met Gly Gly Lys Pro Arg Arg Lys Asn Pro Gln Glu Gly Leu
             420                 425                 430

Tyr Asn Glu Leu Gln Lys Asp Lys Met Ala Glu Ala Tyr Ser Glu Ile
         435                 440                 445

Gly Met Lys Gly Glu Arg Arg Arg Gly Lys Gly His Asp Gly Leu Tyr
```

```
                450             455             460
Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 14
<211> LENGTH: 880
<212> TYPE: PRT
<213> ORGANISM: Artificial Sequence
<220> FEATURE:
<223> OTHER INFORMATION: the amino acid sequence of HER2-CXCR5 CAR

<400> SEQUENCE: 14

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Val Asn Thr Ala Val Ala Trp Tyr Gln Gln Lys Pro Gly Lys Ala
    50                  55                  60

Pro Lys Leu Leu Ile Tyr Ser Ala Ser Phe Leu Tyr Ser Gly Val Pro
65                  70                  75                  80

Ser Arg Phe Ser Gly Ser Arg Ser Gly Thr Asp Phe Thr Leu Thr Ile
                85                  90                  95

Ser Ser Leu Gln Pro Glu Asp Phe Ala Thr Tyr Tyr Cys Gln Gln His
            100                 105                 110

Tyr Thr Thr Pro Pro Thr Phe Gly Gln Gly Thr Lys Val Glu Ile Lys
        115                 120                 125

Gly Gly Gly Gly Ser Gly Gly Gly Ser Gly Gly Gly Ser Glu
    130                 135                 140

Val Gln Leu Val Glu Ser Gly Gly Gly Leu Val Gln Pro Gly Gly Ser
145                 150                 155                 160

Leu Arg Leu Ser Cys Ala Ala Ser Gly Phe Asn Ile Lys Asp Thr Tyr
                165                 170                 175

Ile His Trp Val Arg Gln Ala Pro Gly Lys Gly Leu Glu Trp Val Ala
            180                 185                 190

Arg Ile Tyr Pro Thr Asn Gly Tyr Thr Arg Tyr Ala Asp Ser Val Lys
        195                 200                 205

Gly Arg Phe Thr Ile Ser Ala Asp Thr Ser Lys Asn Thr Ala Tyr Leu
    210                 215                 220

Gln Met Asn Ser Leu Arg Ala Glu Asp Thr Ala Val Tyr Tyr Cys Ser
225                 230                 235                 240

Arg Trp Gly Gly Asp Gly Phe Tyr Ala Met Asp Tyr Trp Gly Gln Gly
                245                 250                 255

Thr Leu Val Thr Val Ser Ser Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
```

```
                       325                 330                 335
Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
            355                 360                 365

Glu Gly Gly Cys Glu Leu Arg Val Lys Phe Ser Arg Ser Ala Asp Ala
            370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
            435                 440                 445

Gly Met Lys Gly Glu Arg Arg Arg Gly Lys Gly His Asp Gly Leu Tyr
            450                 455                 460

Gln Gly Leu Ser Thr Ala Thr Lys Asp Thr Tyr Asp Ala Leu His Met
465                 470                 475                 480

Gln Ala Leu Pro Pro Arg Ala Ser Arg Gly Glu Gly Arg Gly Ser Leu
                485                 490                 495

Leu Thr Cys Gly Asp Val Glu Glu Asn Pro Gly Pro Met Asn Tyr Pro
            500                 505                 510

Leu Thr Leu Glu Met Asp Leu Glu Asn Leu Glu Asp Leu Phe Trp Glu
            515                 520                 525

Leu Asp Arg Leu Asp Asn Tyr Asn Asp Thr Ser Leu Val Glu Asn His
            530                 535                 540

Leu Cys Pro Ala Thr Glu Gly Pro Leu Met Ala Ser Phe Lys Ala Val
545                 550                 555                 560

Phe Val Pro Val Ala Tyr Ser Leu Ile Phe Leu Leu Gly Val Ile Gly
                565                 570                 575

Asn Val Leu Val Leu Val Ile Leu Glu Arg His Arg Gln Thr Arg Ser
            580                 585                 590

Ser Thr Glu Thr Phe Leu Phe His Leu Ala Val Ala Asp Leu Leu Leu
            595                 600                 605

Val Phe Ile Leu Pro Phe Ala Val Ala Glu Gly Ser Val Gly Trp Val
            610                 615                 620

Leu Gly Thr Phe Leu Cys Lys Thr Val Ile Ala Leu His Lys Val Asn
625                 630                 635                 640

Phe Tyr Cys Ser Ser Leu Leu Leu Ala Cys Ile Ala Val Asp Arg Tyr
                645                 650                 655

Leu Ala Ile Val His Ala Val His Ala Tyr Arg His Arg Arg Leu Leu
            660                 665                 670

Ser Ile His Ile Thr Cys Gly Thr Ile Trp Leu Val Gly Phe Leu Leu
            675                 680                 685

Ala Leu Pro Glu Ile Leu Phe Ala Lys Val Ser Gln Gly His His Asn
            690                 695                 700

Asn Ser Leu Pro Arg Cys Thr Phe Ser Gln Glu Asn Gln Ala Glu Thr
705                 710                 715                 720

His Ala Trp Phe Thr Ser Arg Phe Leu Tyr His Val Ala Gly Phe Leu
                725                 730                 735

Leu Pro Met Leu Val Met Gly Trp Cys Tyr Val Gly Val Val His Arg
            740                 745                 750
```

Leu Arg Gln Ala Gln Arg Arg Pro Gln Arg Gln Lys Ala Val Arg Val
            755                 760                 765

Ala Ile Leu Val Thr Ser Ile Phe Phe Leu Cys Trp Ser Pro Tyr His
        770                 775                 780

Ile Val Ile Phe Leu Asp Thr Leu Ala Arg Leu Lys Ala Val Asp Asn
785                 790                 795                 800

Thr Cys Lys Leu Asn Gly Ser Leu Pro Val Ala Ile Thr Met Cys Glu
                805                 810                 815

Phe Leu Gly Leu Ala His Cys Cys Leu Asn Pro Met Leu Tyr Thr Phe
                820                 825                 830

Ala Gly Val Lys Phe Arg Ser Asp Leu Ser Arg Leu Leu Thr Lys Leu
                835                 840                 845

Gly Cys Thr Gly Pro Ala Ser Leu Cys Gln Leu Phe Pro Gly Trp Arg
            850                 855                 860

Arg Ser Ser Leu Ser Glu Ser Glu Asn Ala Thr Ser Leu Thr Thr Phe
865                 870                 875                 880

<210> SEQ ID NO 15
<211> LENGTH: 485
<212> TYPE: PRT
<213> ORGANISM: Artificial Sequence
<220> FEATURE:
<223> OTHER INFORMATION: the amino acid sequence of GD2-CAR

<400> SEQUENCE: 15

Met Ala Leu Pro Val Thr Ala Leu Leu Leu Pro Leu Ala Leu Leu Leu
1               5                   10                  15

His Ala Ala Arg Pro Asp Val Val Met Thr Gln Thr Pro Leu Ser Leu
                20                  25                  30

Pro Val Ser Leu Gly Asp Gln Ala Ser Ile Ser Cys Arg Ser Ser Gln
            35                  40                  45

Ser Leu Val His Arg Asn Gly Asn Thr Tyr Leu His Trp Tyr Leu Gln
        50                  55                  60

Lys Pro Gly Gln Ser Pro Lys Leu Leu Ile His Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
                100                 105                 110

Phe Cys Ser Gln Ser Thr His Val Pro Pro Leu Thr Phe Gly Ala Gly
            115                 120                 125

Thr Lys Leu Glu Leu Lys Gly Gly Gly Gly Ser Gly Gly Gly Gly Ser
        130                 135                 140

Gly Gly Gly Gly Ser Glu Val Gln Leu Leu Gln Ser Gly Pro Glu Leu
145                 150                 155                 160

Glu Lys Pro Ser Ala Ser Val Met Ile Ser Cys Lys Ala Ser Gly Ser
                165                 170                 175

Ser Phe Thr Gly Tyr Asn Met Asn Trp Val Arg Gln Asn Ile Gly Lys
                180                 185                 190

Ser Leu Glu Trp Ile Gly Ala Ile Asp Pro Tyr Tyr Gly Gly Thr Ser
            195                 200                 205

Tyr Asn Gln Lys Phe Lys Gly Arg Ala Thr Leu Thr Val Asp Lys Ser
        210                 215                 220

Ser Ser Thr Ala Tyr Met His Leu Lys Ser Leu Thr Ser Glu Asp Ser
225                 230                 235                 240

```
Ala Val Tyr Tyr Cys Val Ser Gly Met Glu Tyr Trp Gly Gln Gly Thr
            245                 250                 255

Ser Val Thr Val Ser Ser Thr Thr Thr Pro Ala Pro Arg Pro Pro Thr
        260                 265                 270

Pro Ala Pro Thr Ile Ala Ser Gln Pro Leu Ser Leu Arg Pro Glu Ala
            275                 280                 285

Cys Arg Pro Ala Ala Gly Gly Ala Val His Thr Arg Gly Leu Asp Phe
290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 16
<211> LENGTH: 879
<212> TYPE: PRT
<213> ORGANISM: Artificial Sequence
<220> FEATURE:
<223> OTHER INFORMATION: the amino acid sequence of GD2-CXCR5 CAR

<400> SEQUENCE: 16

Met Ala Leu Pro Val Thr Ala Leu Leu Leu Pro Leu Ala Leu Leu Leu
1               5                   10                  15

His Ala Ala Arg Pro Asp Val Val Met Thr Gln Thr Pro Leu Ser Leu
            20                  25                  30

Pro Val Ser Leu Gly Asp Gln Ala Ser Ile Ser Cys Arg Ser Ser Gln
        35                  40                  45

Ser Leu Val His Arg Asn Gly Asn Thr Tyr Leu His Trp Tyr Leu Gln
    50                  55                  60

Lys Pro Gly Gln Ser Pro Lys Leu Leu Ile His Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Leu Gly Val Tyr
            100                 105                 110
```

-continued

```
Phe Cys Ser Gln Ser Thr His Val Pro Pro Leu Thr Phe Gly Ala Gly
            115                 120                 125

Thr Lys Leu Glu Leu Lys Gly Gly Gly Ser Gly Gly Gly Gly Ser
        130                 135                 140

Gly Gly Gly Ser Glu Val Gln Leu Gln Ser Gly Pro Glu Leu
145                 150                 155                 160

Glu Lys Pro Ser Ala Ser Val Met Ile Ser Cys Lys Ala Ser Gly Ser
                165                 170                 175

Ser Phe Thr Gly Tyr Asn Met Asn Trp Val Arg Gln Asn Ile Gly Lys
            180                 185                 190

Ser Leu Glu Trp Ile Gly Ala Ile Asp Pro Tyr Tyr Gly Gly Thr Ser
        195                 200                 205

Tyr Asn Gln Lys Phe Lys Gly Arg Ala Thr Leu Thr Val Asp Lys Ser
    210                 215                 220

Ser Ser Thr Ala Tyr Met His Leu Lys Ser Leu Thr Ser Glu Asp Ser
225                 230                 235                 240

Ala Val Tyr Tyr Cys Val Ser Gly Met Glu Tyr Trp Gly Gln Gly Thr
                245                 250                 255

Ser Val Thr Val Ser Ser Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg Ala Ser Arg Gly Glu Gly Arg Gly Ser Leu Leu
                485                 490                 495

Thr Cys Gly Asp Val Glu Glu Asn Pro Gly Pro Met Asn Tyr Pro Leu
            500                 505                 510

Thr Leu Glu Met Asp Leu Glu Asn Leu Glu Asp Leu Phe Trp Glu Leu
        515                 520                 525
```

```
Asp Arg Leu Asp Asn Tyr Asn Asp Thr Ser Leu Val Glu Asn His Leu
            530                 535                 540
Cys Pro Ala Thr Glu Gly Pro Leu Met Ala Ser Phe Lys Ala Val Phe
545                 550                 555                 560
Val Pro Val Ala Tyr Ser Leu Ile Phe Leu Leu Gly Val Ile Gly Asn
                565                 570                 575
Val Leu Val Leu Val Ile Leu Glu Arg His Arg Gln Thr Arg Ser Ser
            580                 585                 590
Thr Glu Thr Phe Leu Phe His Leu Ala Val Ala Asp Leu Leu Leu Val
                595                 600                 605
Phe Ile Leu Pro Phe Ala Val Ala Glu Gly Ser Val Gly Trp Val Leu
610                 615                 620
Gly Thr Phe Leu Cys Lys Thr Val Ile Ala Leu His Lys Val Asn Phe
625                 630                 635                 640
Tyr Cys Ser Ser Leu Leu Leu Ala Cys Ile Ala Val Asp Arg Tyr Leu
                645                 650                 655
Ala Ile Val His Ala Val His Ala Tyr Arg His Arg Arg Leu Leu Ser
            660                 665                 670
Ile His Ile Thr Cys Gly Thr Ile Trp Leu Val Gly Phe Leu Leu Ala
            675                 680                 685
Leu Pro Glu Ile Leu Phe Ala Lys Val Ser Gln Gly His His Asn Asn
690                 695                 700
Ser Leu Pro Arg Cys Thr Phe Ser Gln Glu Asn Gln Ala Glu Thr His
705                 710                 715                 720
Ala Trp Phe Thr Ser Arg Phe Leu Tyr His Val Ala Gly Phe Leu Leu
                725                 730                 735
Pro Met Leu Val Met Gly Trp Cys Tyr Val Gly Val Val His Arg Leu
            740                 745                 750
Arg Gln Ala Gln Arg Arg Pro Gln Arg Gln Lys Ala Val Arg Val Ala
            755                 760                 765
Ile Leu Val Thr Ser Ile Phe Phe Leu Cys Trp Ser Pro Tyr His Ile
            770                 775                 780
Val Ile Phe Leu Asp Thr Leu Ala Arg Leu Lys Ala Val Asp Asn Thr
785                 790                 795                 800
Cys Lys Leu Asn Gly Ser Leu Pro Val Ala Ile Thr Met Cys Glu Phe
                805                 810                 815
Leu Gly Leu Ala His Cys Cys Leu Asn Pro Met Leu Tyr Thr Phe Ala
                820                 825                 830
Gly Val Lys Phe Arg Ser Asp Leu Ser Arg Leu Leu Thr Lys Leu Gly
            835                 840                 845
Cys Thr Gly Pro Ala Ser Leu Cys Gln Leu Phe Pro Gly Trp Arg Arg
850                 855                 860
Ser Ser Leu Ser Glu Ser Glu Asn Ala Thr Ser Leu Thr Thr Phe
865                 870                 875

<210> SEQ ID NO 17
<211> LENGTH: 486
<212> TYPE: PRT
<213> ORGANISM: Artificial Sequence
<220> FEATURE:
<223> OTHER INFORMATION: the amino acid sequence of GPC3-CAR

<400> SEQUENCE: 17

Met Ala Leu Pro Val Thr Ala Leu Leu Leu Pro Leu Ala Leu Leu Leu
1               5                   10                  15
```

-continued

His Ala Ala Arg Pro Asp Ile Val Met Thr Gln Thr Pro Leu Ser Leu
            20                  25                  30

Pro Val Thr Pro Gly Glu Pro Ala Ser Ile Ser Cys Arg Ser Ser Gln
        35                  40                  45

Ser Leu Val His Ser Asn Gly Asn Thr Tyr Leu Gln Trp Tyr Leu Gln
    50                  55                  60

Lys Pro Gly Gln Ser Pro Gln Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Ser Gln Ser Ile Tyr Val Pro Tyr Thr Phe Gly Gln Gly Thr
        115                 120                 125

Lys Leu Glu Ile Lys Gly Gly Gly Gly Ser Gly Gly Gly Gly Ser Gly
    130                 135                 140

Gly Gly Ser Glu Val Gln Leu Val Gln Ser Gly Ala Glu Val Lys
145                 150                 155                 160

Lys Pro Gly Ala Ser Val Lys Val Ser Cys Lys Ala Ser Gly Tyr Thr
                165                 170                 175

Phe Ser Asp Tyr Glu Met His Trp Val Arg Gln Ala Pro Gly Gln Gly
            180                 185                 190

Leu Glu Trp Met Gly Ala Ile His Pro Gly Ser Gly Asp Thr Ala Tyr
        195                 200                 205

Asn Gln Arg Phe Lys Gly Arg Val Thr Ile Thr Ala Asp Lys Ser Thr
    210                 215                 220

Ser Thr Ala Tyr Met Glu Leu Ser Ser Leu Arg Ser Glu Asp Thr Ala
225                 230                 235                 240

Val Tyr Tyr Cys Ala Arg Phe Tyr Ser Tyr Ala Tyr Trp Gly Gln Gly
                245                 250                 255

Thr Leu Val Thr Val Ser Ala Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile

```
                    435                 440                 445
Gly Met Lys Gly Glu Arg Arg Gly Lys Gly His Asp Gly Leu Tyr
    450                 455                 460
Gln Gly Leu Ser Thr Ala Thr Lys Asp Thr Tyr Asp Ala Leu His Met
465                 470                 475                 480
Gln Ala Leu Pro Pro Arg
                485

<210> SEQ ID NO 18
<211> LENGTH: 880
<212> TYPE: PRT
<213> ORGANISM: Artificial Sequence
<220> FEATURE:
<223> OTHER INFORMATION: the amino acid sequence of GPC3-CXCR5 CAR

<400> SEQUENCE: 18

Met Ala Leu Pro Val Thr Ala Leu Leu Leu Pro Leu Ala Leu Leu Leu
1               5                   10                  15
His Ala Ala Arg Pro Asp Ile Val Met Thr Gln Thr Pro Leu Ser Leu
                20                  25                  30
Pro Val Thr Pro Gly Glu Pro Ala Ser Ile Ser Cys Arg Ser Ser Gln
            35                  40                  45
Ser Leu Val His Ser Asn Gly Asn Thr Tyr Leu Gln Trp Tyr Leu Gln
        50                  55                  60
Lys Pro Gly Gln Ser Pro Gln Leu Leu Ile Tyr Lys Val Ser Asn Arg
65                  70                  75                  80
Phe Ser Gly Val Pro Asp Arg Phe Ser Gly Ser Gly Ser Gly Thr Asp
                85                  90                  95
Phe Thr Leu Lys Ile Ser Arg Val Glu Ala Glu Asp Val Gly Val Tyr
                100                 105                 110
Tyr Cys Ser Gln Ser Ile Tyr Val Pro Tyr Thr Phe Gly Gln Gly Thr
            115                 120                 125
Lys Leu Glu Ile Lys Gly Gly Gly Gly Ser Gly Gly Gly Ser Gly
        130                 135                 140
Gly Gly Gly Ser Glu Val Gln Leu Val Gln Ser Gly Ala Glu Val Lys
145                 150                 155                 160
Lys Pro Gly Ala Ser Val Lys Val Ser Cys Lys Ala Ser Gly Tyr Thr
                165                 170                 175
Phe Ser Asp Tyr Glu Met His Trp Val Arg Gln Ala Pro Gly Gln Gly
                180                 185                 190
Leu Glu Trp Met Gly Ala Ile His Pro Gly Ser Gly Asp Thr Ala Tyr
            195                 200                 205
Asn Gln Arg Phe Lys Gly Arg Val Thr Ile Thr Ala Asp Lys Ser Thr
        210                 215                 220
Ser Thr Ala Tyr Met Glu Leu Ser Ser Leu Arg Ser Glu Asp Thr Ala
225                 230                 235                 240
Val Tyr Tyr Cys Ala Arg Phe Tyr Ser Tyr Ala Tyr Trp Gly Gln Gly
                245                 250                 255
Thr Leu Val Thr Val Ser Ala Thr Thr Thr Pro Ala Pro Arg Pro Pro
                260                 265                 270
Thr Pro Ala Pro Thr Ile Ala Ser Gln Pro Leu Ser Leu Arg Pro Glu
            275                 280                 285
Ala Cys Arg Pro Ala Ala Gly Gly Ala Val His Thr Arg Gly Leu Asp
        290                 295                 300
Phe Ala Cys Asp Ile Tyr Ile Trp Ala Pro Leu Ala Gly Thr Cys Gly
```

```
            305                 310                 315                 320
    Val Leu Leu Leu Ser Leu Val Ile Thr Leu Tyr Cys Lys Arg Gly Arg
                    325                 330                 335

Lys Lys Leu Leu Tyr Ile Phe Lys Gln Pro Phe Met Arg Pro Val Gln
                    340                 345                 350

Thr Thr Gln Glu Glu Asp Gly Cys Ser Cys Arg Phe Pro Glu Glu Glu
                    355                 360                 365

Glu Gly Gly Cys Glu Leu Arg Val Lys Phe Ser Arg Ser Ala Asp Ala
                    370                 375                 380

Pro Ala Tyr Gln Gln Gly Gln Asn Gln Leu Tyr Asn Glu Leu Asn Leu
    385                 390                 395                 400

Gly Arg Arg Glu Glu Tyr Asp Val Leu Asp Lys Arg Arg Gly Arg Asp
                    405                 410                 415

Pro Glu Met Gly Gly Lys Pro Arg Arg Lys Asn Pro Gln Glu Gly Leu
                    420                 425                 430

Tyr Asn Glu Leu Gln Lys Asp Lys Met Ala Glu Ala Tyr Ser Glu Ile
                    435                 440                 445

Gly Met Lys Gly Glu Arg Arg Arg Gly Lys Gly His Asp Gly Leu Tyr
                    450                 455                 460

Gln Gly Leu Ser Thr Ala Thr Lys Asp Thr Tyr Asp Ala Leu His Met
    465                 470                 475                 480

Gln Ala Leu Pro Pro Arg Ala Ser Arg Gly Glu Gly Arg Gly Ser Leu
                    485                 490                 495

Leu Thr Cys Gly Asp Val Glu Glu Asn Pro Gly Pro Met Asn Tyr Pro
                    500                 505                 510

Leu Thr Leu Glu Met Asp Leu Glu Asn Leu Glu Asp Leu Phe Trp Glu
                    515                 520                 525

Leu Asp Arg Leu Asp Asn Tyr Asn Asp Thr Ser Leu Val Glu Asn His
                    530                 535                 540

Leu Cys Pro Ala Thr Glu Gly Pro Leu Met Ala Ser Phe Lys Ala Val
    545                 550                 555                 560

Phe Val Pro Val Ala Tyr Ser Leu Ile Phe Leu Leu Gly Val Ile Gly
                    565                 570                 575

Asn Val Leu Val Leu Val Ile Leu Glu Arg His Arg Gln Thr Arg Ser
                    580                 585                 590

Ser Thr Glu Thr Phe Leu Phe His Leu Ala Val Ala Asp Leu Leu Leu
                    595                 600                 605

Val Phe Ile Leu Pro Phe Ala Val Ala Glu Gly Ser Val Gly Trp Val
                    610                 615                 620

Leu Gly Thr Phe Leu Cys Lys Thr Val Ile Ala Leu His Lys Val Asn
    625                 630                 635                 640

Phe Tyr Cys Ser Ser Leu Leu Leu Ala Cys Ile Ala Val Asp Arg Tyr
                    645                 650                 655

Leu Ala Ile Val His Ala Val His Ala Tyr Arg His Arg Arg Leu Leu
                    660                 665                 670

Ser Ile His Ile Thr Cys Gly Thr Ile Trp Leu Val Gly Phe Leu Leu
                    675                 680                 685

Ala Leu Pro Glu Ile Leu Phe Ala Lys Val Ser Gln Gly His His Asn
                    690                 695                 700

Asn Ser Leu Pro Arg Cys Thr Phe Ser Gln Glu Asn Gln Ala Glu Thr
    705                 710                 715                 720

His Ala Trp Phe Thr Ser Arg Phe Leu Tyr His Val Ala Gly Phe Leu
                    725                 730                 735
```

```
Leu Pro Met Leu Val Met Gly Trp Cys Tyr Val Gly Val Val His Arg
            740                 745                 750

Leu Arg Gln Ala Gln Arg Arg Pro Gln Arg Gln Lys Ala Val Arg Val
            755                 760                 765

Ala Ile Leu Val Thr Ser Ile Phe Phe Leu Cys Trp Ser Pro Tyr His
770                 775                 780

Ile Val Ile Phe Leu Asp Thr Leu Ala Arg Leu Lys Ala Val Asp Asn
785                 790                 795                 800

Thr Cys Lys Leu Asn Gly Ser Leu Pro Val Ala Ile Thr Met Cys Glu
                805                 810                 815

Phe Leu Gly Leu Ala His Cys Cys Leu Asn Pro Met Leu Tyr Thr Phe
            820                 825                 830

Ala Gly Val Lys Phe Arg Ser Asp Leu Ser Arg Leu Leu Thr Lys Leu
            835                 840                 845

Gly Cys Thr Gly Pro Ala Ser Leu Cys Gln Leu Phe Pro Gly Trp Arg
850                 855                 860

Arg Ser Ser Leu Ser Glu Ser Glu Asn Ala Thr Ser Leu Thr Thr Phe
865                 870                 875                 880

<210> SEQ ID NO 19
<211> LENGTH: 488
<212> TYPE: PRT
<213> ORGANISM: Artificial Sequence
<220> FEATURE:
<223> OTHER INFORMATION: the amino acid sequence of MUC1-CAR

<400> SEQUENCE: 19

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Ser Ser Leu
            20                  25                  30

Thr Val Thr Ala Gly Glu Lys Val Thr Met Ile Cys Lys Ser Ser Gln
        35                  40                  45

Ser Leu Leu Asn Ser Gly Asp Gln Lys Asn Tyr Leu Thr Trp Tyr Gln
    50                  55                  60

Gln Lys Pro Gly Gln Pro Pro Lys Leu Leu Ile Phe Trp Ala Ser Thr
65                  70                  75                  80

Arg Glu Ser Gly Val Pro Asp Arg Phe Thr Gly Ser Gly Ser Gly Thr
                85                  90                  95

Asp Phe Thr Leu Thr Ile Ser Ser Val Gln Ala Glu Asp Leu Ala Val
            100                 105                 110

Tyr Tyr Cys Gln Asn Asp Tyr Ser Tyr Pro Leu Thr Phe Gly Ala Gly
        115                 120                 125

Thr Lys Leu Glu Leu Lys Gly Gly Gly Gly Ser Gly Gly Gly Gly Ser
    130                 135                 140

Gly Gly Gly Gly Ser Gln Val Gln Leu Gln Gln Ser Asp Ala Glu Leu
145                 150                 155                 160

Val Lys Pro Gly Ser Ser Val Lys Ile Ser Cys Lys Ala Ser Gly Tyr
                165                 170                 175

Thr Phe Thr Asp His Ala Ile His Trp Val Lys Gln Lys Pro Glu Gln
            180                 185                 190

Gly Leu Glu Trp Ile Gly His Phe Ser Pro Gly Asn Thr Asp Ile Lys
        195                 200                 205

Tyr Asn Asp Lys Phe Lys Gly Lys Ala Thr Leu Thr Val Asp Arg Ser
    210                 215                 220
```

```
Ser Ser Thr Ala Tyr Met Gln Leu Asn Ser Leu Thr Ser Glu Asp Ser
225                 230                 235                 240

Ala Val Tyr Phe Cys Lys Thr Ser Thr Phe Phe Asp Tyr Trp Gly
                245                 250                 255

Gln Gly Thr Thr Leu Thr Val Ser Ser Thr Thr Thr Pro Ala Pro Arg
                260                 265                 270

Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
            290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
                340                 345                 350

Val Gln Thr Thr Gln Glu Glu Asp Gly Cys Ser Cys Arg Phe Pro Glu
                355                 360                 365

Glu Glu Glu Gly Gly Cys Glu Leu Arg Val Lys Phe Ser Arg Ser Ala
370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
                420                 425                 430

Gly Leu Tyr Asn Glu Leu Gln Lys Asp Lys Met Ala Glu Ala Tyr Ser
                435                 440                 445

Glu Ile Gly Met Lys Gly Glu Arg Arg Arg Gly Lys Gly His Asp Gly
                450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 20
<211> LENGTH: 882
<212> TYPE: PRT
<213> ORGANISM: Artificial Sequence
<220> FEATURE:
<223> OTHER INFORMATION: the amino acid sequence of MUC1-CXCR5 CAR

<400> SEQUENCE: 20

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Ser Ser Leu
                20                  25                  30

Thr Val Thr Ala Gly Glu Lys Val Thr Met Ile Cys Lys Ser Ser Gln
            35                  40                  45

Ser Leu Leu Asn Ser Gly Asp Gln Lys Asn Tyr Leu Thr Trp Tyr Gln
        50                  55                  60

Gln Lys Pro Gly Gln Pro Pro Lys Leu Leu Ile Phe Trp Ala Ser Thr
65                  70                  75                  80

Arg Glu Ser Gly Val Pro Asp Arg Phe Thr Gly Ser Gly Ser Gly Thr
                85                  90                  95
```

```
Asp Phe Thr Leu Thr Ile Ser Ser Val Gln Ala Glu Asp Leu Ala Val
            100                 105                 110

Tyr Tyr Cys Gln Asn Asp Tyr Ser Tyr Pro Leu Thr Phe Gly Ala Gly
            115                 120                 125

Thr Lys Leu Glu Leu Lys Gly Gly Gly Ser Gly Gly Gly Gly Ser
130                 135                 140

Gly Gly Gly Ser Gln Val Gln Leu Gln Gln Ser Asp Ala Glu Leu
145                 150                 155                 160

Val Lys Pro Gly Ser Ser Val Lys Ile Ser Cys Lys Ala Ser Gly Tyr
                165                 170                 175

Thr Phe Thr Asp His Ala Ile His Trp Val Lys Gln Lys Pro Glu Gln
            180                 185                 190

Gly Leu Glu Trp Ile Gly His Phe Ser Pro Gly Asn Thr Asp Ile Lys
            195                 200                 205

Tyr Asn Asp Lys Phe Lys Gly Lys Ala Thr Leu Thr Val Asp Arg Ser
210                 215                 220

Ser Ser Thr Ala Tyr Met Gln Leu Asn Ser Leu Thr Ser Glu Asp Ser
225                 230                 235                 240

Ala Val Tyr Phe Cys Lys Thr Ser Thr Phe Phe Phe Asp Tyr Trp Gly
                245                 250                 255

Gln Gly Thr Thr Leu Thr Val Ser Ser Thr Thr Thr Pro Ala Pro Arg
            260                 265                 270

Pro Pro Thr Pro Ala Pro Thr Ile Ala Ser Gln Pro Leu Ser Leu Arg
            275                 280                 285

Pro Glu Ala Cys Arg Pro Ala Ala Gly Gly Ala Val His Thr Arg Gly
            290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
            355                 360                 365

Glu Glu Glu Gly Gly Cys Glu Leu Arg Val Lys Phe Ser Arg Ser Ala
            370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
            450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg Ala Ser Arg Gly Glu Gly Arg Gly
                485                 490                 495

Ser Leu Leu Thr Cys Gly Asp Val Glu Glu Asn Pro Gly Pro Met Asn
            500                 505                 510
```

```
Tyr Pro Leu Thr Leu Glu Met Asp Leu Glu Asn Leu Glu Asp Leu Phe
            515                 520                 525

Trp Glu Leu Asp Arg Leu Asp Asn Tyr Asn Asp Thr Ser Leu Val Glu
530                 535                 540

Asn His Leu Cys Pro Ala Thr Glu Gly Pro Leu Met Ala Ser Phe Lys
545                 550                 555                 560

Ala Val Phe Val Pro Val Ala Tyr Ser Leu Ile Phe Leu Leu Gly Val
                565                 570                 575

Ile Gly Asn Val Leu Val Leu Val Ile Leu Glu Arg His Arg Gln Thr
            580                 585                 590

Arg Ser Ser Thr Glu Thr Phe Leu Phe His Leu Ala Val Ala Asp Leu
595                 600                 605

Leu Leu Val Phe Ile Leu Pro Phe Ala Val Ala Glu Gly Ser Val Gly
610                 615                 620

Trp Val Leu Gly Thr Phe Leu Cys Lys Thr Val Ile Ala Leu His Lys
625                 630                 635                 640

Val Asn Phe Tyr Cys Ser Ser Leu Leu Leu Ala Cys Ile Ala Val Asp
                645                 650                 655

Arg Tyr Leu Ala Ile Val His Ala Val His Ala Tyr Arg His Arg Arg
            660                 665                 670

Leu Leu Ser Ile His Ile Thr Cys Gly Thr Ile Trp Leu Val Gly Phe
675                 680                 685

Leu Leu Ala Leu Pro Glu Ile Leu Phe Ala Lys Val Ser Gln Gly His
            690                 695                 700

His Asn Asn Ser Leu Pro Arg Cys Thr Phe Ser Gln Glu Asn Gln Ala
705                 710                 715                 720

Glu Thr His Ala Trp Phe Thr Ser Arg Phe Leu Tyr His Val Ala Gly
                725                 730                 735

Phe Leu Leu Pro Met Leu Val Met Gly Trp Cys Tyr Val Gly Val Val
            740                 745                 750

His Arg Leu Arg Gln Ala Gln Arg Arg Pro Gln Arg Gln Lys Ala Val
755                 760                 765

Arg Val Ala Ile Leu Val Thr Ser Ile Phe Phe Leu Cys Trp Ser Pro
770                 775                 780

Tyr His Ile Val Ile Phe Leu Asp Thr Leu Ala Arg Leu Lys Ala Val
785                 790                 795                 800

Asp Asn Thr Cys Lys Leu Asn Gly Ser Leu Pro Val Ala Ile Thr Met
                805                 810                 815

Cys Glu Phe Leu Gly Leu Ala His Cys Cys Leu Asn Pro Met Leu Tyr
            820                 825                 830

Thr Phe Ala Gly Val Lys Phe Arg Ser Asp Leu Ser Arg Leu Leu Thr
835                 840                 845

Lys Leu Gly Cys Thr Gly Pro Ala Ser Leu Cys Gln Leu Phe Pro Gly
850                 855                 860

Trp Arg Arg Ser Ser Leu Ser Glu Ser Glu Asn Ala Thr Ser Leu Thr
865                 870                 875                 880

Thr Phe

<210> SEQ ID NO 21
<211> LENGTH: 482
<212> TYPE: PRT
<213> ORGANISM: Artificial Sequence
<220> FEATURE:
<223> OTHER INFORMATION: the amino acid sequence of PMSA-CAR
```

<400> SEQUENCE: 21

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Thr Ser Val Gly Asp Arg Val Thr Leu Thr Cys Lys Ala Ser
        35                  40                  45

Gln Asp Val Gly Thr Ala Val Asp Trp Tyr Gln Lys Pro Gly Pro
    50                  55                  60

Ser Pro Lys Leu Leu Ile Tyr Trp Ala Ser Thr Arg His Thr Gly Ile
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Asp Tyr Tyr Cys Gln Gln
            100                 105                 110

Tyr Asn Ser Tyr Pro Leu Thr Phe Gly Pro Gly Thr Lys Val Asp Ile
        115                 120                 125

Lys Gly Gly Gly Gly Ser Gly Gly Gly Gly Ser Gly Gly Gly Gly Ser
    130                 135                 140

Glu Val Gly Leu Val Gln Ser Gly Pro Glu Val Lys Lys Pro Gly Ala
145                 150                 155                 160

Thr Val Lys Ile Ser Cys Lys Thr Ser Gly Tyr Thr Phe Thr Glu Tyr
                165                 170                 175

Thr Ile His Trp Val Lys Gln Ala Pro Gly Lys Gly Leu Glu Trp Ile
            180                 185                 190

Gly Asn Ile Asn Pro Asn Asn Gly Gly Thr Thr Tyr Asn Gln Lys Phe
        195                 200                 205

Glu Asp Lys Ala Thr Leu Thr Val Asp Lys Ser Thr Asp Thr Ala Tyr
    210                 215                 220

Met Glu Leu Ser Ser Leu Arg Ser Glu Asp Thr Ala Val Tyr Tyr Cys
225                 230                 235                 240

Ala Ala Gly Trp Asn Phe Asp Tyr Trp Gly Gln Gly Thr Leu Leu Thr
                245                 250                 255

Val Ser Ser Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
        355                 360                 365

Glu Leu Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415
```

```
Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
450                 455                 460

Thr Ala Thr Lys Asp Thr Tyr Asp Ala Leu His Met Gln Ala Leu Pro
465                 470                 475                 480

Pro Arg

<210> SEQ ID NO 22
<211> LENGTH: 876
<212> TYPE: PRT
<213> ORGANISM: Artificial Sequence
<220> FEATURE:
<223> OTHER INFORMATION: the amino acid sequence of PMSA-CXCR5 CAR

<400> SEQUENCE: 22

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Thr Ser Val Gly Asp Arg Val Thr Leu Thr Cys Lys Ala Ser
        35                  40                  45

Gln Asp Val Gly Thr Ala Val Asp Trp Tyr Gln Gln Lys Pro Gly Pro
    50                  55                  60

Ser Pro Lys Leu Leu Ile Tyr Trp Ala Ser Thr Arg His Thr Gly Ile
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Asp Tyr Tyr Cys Gln Gln
            100                 105                 110

Tyr Asn Ser Tyr Pro Leu Thr Phe Gly Pro Gly Thr Lys Val Asp Ile
        115                 120                 125

Lys Gly Gly Gly Gly Ser Gly Gly Gly Ser Gly Gly Gly Gly Ser
    130                 135                 140

Glu Val Gly Leu Val Gln Ser Gly Pro Glu Val Lys Lys Pro Gly Ala
145                 150                 155                 160

Thr Val Lys Ile Ser Cys Lys Thr Ser Gly Tyr Thr Phe Thr Glu Tyr
                165                 170                 175

Thr Ile His Trp Val Lys Gln Ala Pro Gly Lys Gly Leu Glu Trp Ile
            180                 185                 190

Gly Asn Ile Asn Pro Asn Asn Gly Gly Thr Thr Tyr Asn Gln Lys Phe
        195                 200                 205

Glu Asp Lys Ala Thr Leu Thr Val Asp Lys Ser Thr Asp Thr Ala Tyr
    210                 215                 220

Met Glu Leu Ser Ser Leu Arg Ser Glu Asp Thr Ala Val Tyr Tyr Cys
225                 230                 235                 240

Ala Ala Gly Trp Asn Phe Asp Tyr Trp Gly Gln Gly Thr Leu Leu Thr
                245                 250                 255

Val Ser Ser Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285
```

```
Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
        355                 360                 365

Glu Leu Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg Ala Ser Arg Gly Glu Gly Arg Gly Ser Leu Leu Thr Cys Gly
                485                 490                 495

Asp Val Glu Glu Asn Pro Gly Pro Met Asn Tyr Pro Leu Thr Leu Glu
            500                 505                 510

Met Asp Leu Glu Asn Leu Glu Asp Leu Phe Trp Glu Leu Asp Arg Leu
        515                 520                 525

Asp Asn Tyr Asn Asp Thr Ser Leu Val Glu Asn His Leu Cys Pro Ala
    530                 535                 540

Thr Glu Gly Pro Leu Met Ala Ser Phe Lys Ala Val Phe Val Pro Val
545                 550                 555                 560

Ala Tyr Ser Leu Ile Phe Leu Leu Gly Val Ile Gly Asn Val Leu Val
                565                 570                 575

Leu Val Ile Leu Glu Arg His Arg Gln Thr Arg Ser Ser Thr Glu Thr
            580                 585                 590

Phe Leu Phe His Leu Ala Val Ala Asp Leu Leu Leu Val Phe Ile Leu
        595                 600                 605

Pro Phe Ala Val Ala Glu Gly Ser Val Gly Trp Val Leu Gly Thr Phe
    610                 615                 620

Leu Cys Lys Thr Val Ile Ala Leu His Lys Val Asn Phe Tyr Cys Ser
625                 630                 635                 640

Ser Leu Leu Leu Ala Cys Ile Ala Val Asp Arg Tyr Leu Ala Ile Val
                645                 650                 655

His Ala Val His Ala Tyr Arg His Arg Arg Leu Leu Ser Ile His Ile
            660                 665                 670

Thr Cys Gly Thr Ile Trp Leu Val Gly Phe Leu Leu Ala Leu Pro Glu
        675                 680                 685

Ile Leu Phe Ala Lys Val Ser Gln Gly His His Asn Asn Ser Leu Pro
    690                 695                 700

Arg Cys Thr Phe Ser Gln Glu Asn Gln Ala Glu Thr His Ala Trp Phe
```

```
                705                 710                 715                 720
        Thr Ser Arg Phe Leu Tyr His Val Ala Gly Phe Leu Leu Pro Met Leu
                        725                 730                 735

Val Met Gly Trp Cys Tyr Val Gly Val Val His Arg Leu Arg Gln Ala
                        740                 745                 750

Gln Arg Arg Pro Gln Arg Gln Lys Ala Val Arg Val Ala Ile Leu Val
                        755                 760                 765

Thr Ser Ile Phe Phe Leu Cys Trp Ser Pro Tyr His Ile Val Ile Phe
                        770                 775                 780

Leu Asp Thr Leu Ala Arg Leu Lys Ala Val Asp Asn Thr Cys Lys Leu
        785                 790                 795                 800

Asn Gly Ser Leu Pro Val Ala Ile Thr Met Cys Glu Phe Leu Gly Leu
                        805                 810                 815

Ala His Cys Cys Leu Asn Pro Met Leu Tyr Thr Phe Ala Gly Val Lys
                        820                 825                 830

Phe Arg Ser Asp Leu Ser Arg Leu Leu Thr Lys Leu Gly Cys Thr Gly
                        835                 840                 845

Pro Ala Ser Leu Cys Gln Leu Phe Pro Gly Trp Arg Arg Ser Ser Leu
                        850                 855                 860

Ser Glu Ser Glu Asn Ala Thr Ser Leu Thr Thr Phe
        865                 870                 875

<210> SEQ ID NO 23
<211> LENGTH: 22
<212> TYPE: PRT
<213> ORGANISM: Artificial Sequence
<220> FEATURE:
<223> OTHER INFORMATION: the amino acid sequence of T2A

<400> SEQUENCE: 23

Ala Ser Arg Gly Glu Gly Arg Gly Ser Leu Leu Thr Cys Gly Asp Val
1               5                   10                  15

Glu Glu Asn Pro Gly Pro
            20

<210> SEQ ID NO 24
<211> LENGTH: 22
<212> TYPE: PRT
<213> ORGANISM: Artificial Sequence
<220> FEATURE:
<223> OTHER INFORMATION: the amino acid sequence of P2A

<400> SEQUENCE: 24

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 25
<211> LENGTH: 25
<212> TYPE: PRT
<213> ORGANISM: Artificial Sequence
<220> FEATURE:
<223> OTHER INFORMATION: the amino acid sequence of F2A

<400> SEQUENCE: 25

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```

```
<210> SEQ ID NO 26
<211> LENGTH: 21
<212> TYPE: PRT
<213> ORGANISM: Artificial Sequence
<220> FEATURE:
<223> OTHER INFORMATION: the amino acid sequence of E2A

<400> SEQUENCE: 26

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 27
<211> LENGTH: 372
<212> TYPE: PRT
<213> ORGANISM: Artificial Sequence
<220> FEATURE:
<223> OTHER INFORMATION: the amino acid sequence of CXCR5

<400> SEQUENCE: 27

Met Asn Tyr Pro Leu Thr Leu Glu Met Asp Leu Glu Asn Leu Glu Asp
1               5                   10                  15

Leu Phe Trp Glu Leu Asp Arg Leu Asp Asn Tyr Asn Asp Thr Ser Leu
            20                  25                  30

Val Glu Asn His Leu Cys Pro Ala Thr Glu Gly Pro Leu Met Ala Ser
        35                  40                  45

Phe Lys Ala Val Phe Val Pro Val Ala Tyr Ser Leu Ile Phe Leu Leu
    50                  55                  60

Gly Val Ile Gly Asn Val Leu Val Leu Val Ile Leu Glu Arg His Arg
65                  70                  75                  80

Gln Thr Arg Ser Ser Thr Glu Thr Phe Leu Phe His Leu Ala Val Ala
                85                  90                  95

Asp Leu Leu Leu Val Phe Ile Leu Pro Phe Ala Val Ala Glu Gly Ser
            100                 105                 110

Val Gly Trp Val Leu Gly Thr Phe Leu Cys Lys Thr Val Ile Ala Leu
        115                 120                 125

His Lys Val Asn Phe Tyr Cys Ser Ser Leu Leu Leu Ala Cys Ile Ala
    130                 135                 140

Val Asp Arg Tyr Leu Ala Ile Val His Ala Val His Ala Tyr Arg His
145                 150                 155                 160

Arg Arg Leu Leu Ser Ile His Ile Thr Cys Gly Thr Ile Trp Leu Val
                165                 170                 175

Gly Phe Leu Leu Ala Leu Pro Glu Ile Leu Phe Ala Lys Val Ser Gln
            180                 185                 190

Gly His His Asn Asn Ser Leu Pro Arg Cys Thr Phe Ser Gln Glu Asn
        195                 200                 205

Gln Ala Glu Thr His Ala Trp Phe Thr Ser Arg Phe Leu Tyr His Val
    210                 215                 220

Ala Gly Phe Leu Leu Pro Met Leu Val Met Gly Trp Cys Tyr Val Gly
225                 230                 235                 240

Val Val His Arg Leu Arg Gln Ala Gln Arg Arg Pro Gln Arg Gln Lys
                245                 250                 255

Ala Val Arg Val Ala Ile Leu Val Thr Ser Ile Phe Phe Leu Cys Trp
            260                 265                 270

Ser Pro Tyr His Ile Val Ile Phe Leu Asp Thr Leu Ala Arg Leu Lys
```

-continued

```
                275                 280                 285
Ala Val Asp Asn Thr Cys Lys Leu Asn Gly Ser Leu Pro Val Ala Ile
    290                 295                 300

Thr Met Cys Glu Phe Leu Gly Leu Ala His Cys Cys Leu Asn Pro Met
305                 310                 315                 320

Leu Tyr Thr Phe Ala Gly Val Lys Phe Arg Ser Asp Leu Ser Arg Leu
                325                 330                 335

Leu Thr Lys Leu Gly Cys Thr Gly Pro Ala Ser Leu Cys Gln Leu Phe
                340                 345                 350

Pro Gly Trp Arg Arg Ser Ser Leu Ser Glu Ser Glu Asn Ala Thr Ser
                355                 360                 365

Leu Thr Thr Phe
    370

<210> SEQ ID NO 28
<211> LENGTH: 109
<212> TYPE: PRT
<213> ORGANISM: Artificial Sequence
<220> FEATURE:
<223> OTHER INFORMATION: the amino acid sequence of CXCL13

<400> SEQUENCE: 28

Met Lys Phe Ile Ser Thr Ser Leu Leu Leu Met Leu Leu Val Ser Ser
1               5                   10                  15

Leu Ser Pro Val Gln Gly Val Leu Glu Val Tyr Tyr Thr Ser Leu Arg
                20                  25                  30

Cys Arg Cys Val Gln Glu Ser Ser Val Phe Ile Pro Arg Arg Phe Ile
                35                  40                  45

Asp Arg Ile Gln Ile Leu Pro Arg Gly Asn Gly Cys Pro Arg Lys Glu
        50                  55                  60

Ile Ile Val Trp Lys Lys Asn Lys Ser Ile Val Cys Val Asp Pro Gln
65                  70                  75                  80

Ala Glu Trp Ile Gln Arg Met Met Glu Val Leu Arg Lys Arg Ser Ser
                85                  90                  95

Ser Thr Leu Pro Val Pro Val Phe Lys Arg Lys Ile Pro
                100                 105
```

USE OF CHEMOKINE RECEPTOR CXCR5

CROSS-REFERENCE TO RELATED APPLICATIONS

This application is a § 371 national stage of PCT International Application No. PCT/CN2019/124916, filed Dec. 12, 2019, claiming priority of Chinese Patent Application No. 201811643734.6, filed Dec. 29, 2018, the contents of each of which are hereby incorporated by reference into the application.

REFERENCE TO A SEQUENCE LISTING

This application incorporates-by-reference nucleotide and/or amino acid sequences which are present in the file named "200311_5886_91331_Sequence_Listing_SC.txt", which is 134 kilobytes in size, and which was created Mar. 11, 2020 in the IBM-PC machine format, having an operating system compatibility with MS-Windows, which is contained in the text file filed Mar. 11, 2020 as part of this application.

TECHNICAL FIELD

The present disclosure belongs to the field of biotechnology, and relates to use of chemokine receptor CXCR5.

BACKGROUND

In recent years, re-activating the human autoimmune system by blocking the PD-1/PD-L1 signaling pathway has shown potential in the treatment for patients with solid tumors including non-small-cell lung carcinoma. Therefore, targeting cancer cells by using the immune system has also become a potential method for the treatment of solid tumors. Today, although chimeric antigen receptor T cell (CAR-T) therapy has achieved impressive results in the elimination of hematologic cancers, it is generally not so effective against solid tumors. Multiple factors may be the causes of preventing CAR-T from successfully treating solid tumors, including: antigen expression in tumors, wherein both local differentiation and antigen loss can cause the failure of the CAR-T; hypoxic, immunosuppressive tumor microenvironment; and factors such as directional migration of T cells toward tumors. All of the above mentioned factors can affect the therapeutic effect of CAR-T. The modified, re-infused CAR-T cells must be able to pair with a cancer-derived chemokine to successfully reach the location of solid tumors, and must successfully pass through the stromal cells of solid tumors to exhibit tumor antigen-specific cytotoxic killing. Traditional CAR-T is more susceptible to the immunosuppressive microenvironment of solid tumors due to its relative simple design, which limits the application of CAR-T cell therapy technology for solid tumors.

The migration of T cells is primarily dependent on the guide of pairing between cell chemokine and receptor thereof. In recent years, it has been reported that the catalytic factor CXCL13 (also known as B cell chemokine, BLC1) is highly expressed in the tumor tissues of 90% of patients with non-small cell lung carcinoma in Xuanwei City, Yunnan Province, China. In addition, high expression of CXCL13 and receptor CXCR5 is also common in tissues of such as prostate cancer, pancreatic cancer, and breast cancer. CXCR5 is generally expressed in circulating B cells, a small number of CD4+ and CD8+ T cells, and skin-derived migrating dendritic cells. Lymphocytes carrying the CXCR5 receptor can therefore migrate to secondary lymph nodes and tumor sites with high expression of CXCL13. CXCR5+ CD8+ T cells have been found to be enriched in human rectal cancer tissue and adjacent lymph nodes.

At present, most of the traditional CAR-T designs only focus on enhancing T cell activation and proliferation and other functions by optimizing, or increasing, or decreasing chimeric antigen receptor (CAR) regions. However, no enough attention has been paid to how to use the catalytic factor signal to migrate CAR-T towards the target tumor and to avoid immunosuppressive signals (such as PD-1) in the tumor, so that the CAR-T is not so effective for solid tumors. In the domestic and international markets, clinical trials involved in CAR-T cells modified with CXCR receptor also have not been reported.

Therefore, developing a CAR-T cell with high expression of CXCR5 which will guide the migration of modified T cells towards tumors to hopefully solve the problem of poor efficacy of the existing CAR-T therapy for solid tumors has broad application prospects and great market value.

SUMMARY

In view of the deficiencies in the prior art and actual demand, the present disclosure provides use of chemokine receptor CXCR5, wherein a chimeric antigen receptor is prepared by modifying a CXCR receptor by using the tumor-targeting character of CXCR5 which may guide the modified T cells to migrate towards tumors, solving the problem of poor efficacy of the existing CAR-T therapy for solid tumors and exhibiting broad application prospects and great market value.

To achieve this purpose, the present disclosure uses the following technical solutions:

In a first aspect, the present disclosure provides use of chemokine receptor CXCR5 for preparing a chimeric antigen receptor.

Preferably, the chemokine receptor CXCR5 is used for preparing a chimeric antigen receptor targeting a tumor antigen.

In an embodiment, the present disclosure provides a method for preparing a chimeric antigen receptor comprising combining a chimeric antigen receptor with chemokine receptor CXCR5.

In an embodiment, chimeric antigen receptor targets a tumor antigen.

In an embodiment, the tumor antigen is any one or a combination of at least two of the group consisting of CD19, CD20, BCMA, CLL1, EGFR, B7H3, HER2, GD2, GPC3, MUC1 and PSMA.

In the present disclosure, during the long time research and practice, and through the deeply research on the advantages and disadvantages of the CAR-T cell technology, the inventor has found that one of the main reasons for the poor efficacy of CAR-T for treating solid tumors is that the traditional CAR-T is deficient in effective tumor-targeting migration abilities. By searching and studying the latest literature, the chemokine CXCL13 is found to be secreted at high levels in tissues and blood of patients with lung cancer. In the present disclosure, anti-EGFR chimeric antigen receptor T cells expressing high levels of CXCR5 are designed based on the fact that CXCL13 is highly expressed in tumor tissues to solve the defects of previous CAR-T including the poor efficacy in treating solid tumors. A large number of experiments and explorations have demonstrated that the anti-EGFR chimeric antigen receptor T cells expressing high levels of CXCR5 have excellent chemotactic migration ability and can specifically target tumor cells positively expressing EGFR.

In a second aspect, the present disclosure provides a chimeric antigen receptor targeting a tumor antigen, wherein the chimeric antigen receptor is combined with chemokine receptor CXCR5.

In an embodiment, the tumor antigen is any one or a combination of at least two of the group consisting of CD19, CD20, BCMA, CLL1, EGFR, B7H3, HER2, GD2, GPC3, MUC1 and PSMA.

Preferably, the chimeric antigen receptor has the amino acid sequence as shown in any one of SEQ ID NOs. 2, 4, 6, 8, 10, 12, 14, 16, 18, 20 and 22.

In a third aspect, the present disclosure provides a lentivirus, which is obtained by packaging a plasmid comprising the chimeric antigen receptor of the second aspect with a helper plasmid.

In a fourth aspect, the present disclosure provides a pharmaceutical composition, which comprises the chimeric antigen receptor of the second aspect and/or the lentivirus of the third aspect.

Preferably, the pharmaceutical composition further comprises any one or a combination of at least two of the group consisting of a pharmaceutically acceptable carrier, a diluent and an excipient.

In a fifth aspect, the present disclosure provides use of the pharmaceutical composition according to the fourth aspect for the treatment of tumors.

Preferably, the tumor comprises any one or a combination of at least two of the group consisting of gastric cancer, liver cancer, lung cancer, esophageal cancer, cervical cancer, breast cancer, colon cancer, rectal cancer, nasopharyngeal cancer, ovarian cancer, kidney cancer, bladder cancer, thyroid cancer, skin cancer, glioma, neuroblastoma, melanoma and lymphoma.

Chemokines play a vital role in cancer development and metastasis. Many chemokine receptors are expressed on the surface of T cells, such as CCR1, CCR4, CCR6, CCR7, CCR9, CCR10, CXCR4, CXCR5, CXCR6, CX3CR, etc. The expression levels of such receptors may be different in various T cell subtypes and may be enhanced after cell stress, amplification and passage. However, the number of T cells expressing CXCR5 in human peripheral blood is very limited (accounting for about 1-10% of all T cells), the cost for the specific sorting of CXCR5-positive cells is expensive, and the quantity of such cells is far from meeting the demand for CAR-T re-infusion. In addition, CXCL13 is the only ligand for CXCR5 and has a clear chemotaxis mechanism. Therefore, a method involving overexpressing the CXCR5 by viral transfection to enhance the ability of CAR-T to directionally migrate towards tumor sites with high expression of CXCL13, followed by in vitro massive amplification of CAR-T cells and re-infusion of the same, is a feasible method for treating solid tumors with CAR-T.

Compared with the prior art, the present disclosure has the following beneficial effects:

The present disclosure provides an application of the chemokine receptor CXCR5 for preparing chimeric antigen receptor cells, wherein a chimeric antigen receptor is initiatively combined with CXCR5 so that the modified T cells have an enhanced ability to migrate towards tumor, may specifically target tumor cells expressing target proteins, and present strong chemotactic ability and good specificity.

Secondly, by using the fact that chemokine CXCL13 is highly expressed in some patients with lung cancer, the co-expression of CXCR5 may enhance the migration of EGFR CAR-T towards lung cancer sites in vivo and reduce the risk of off-target effects on skin or other tissues, while increasing the migration of CAR-T towards the lymphatic system and inhibiting tumor metastasis to lymph nodes and recurrence. Therefore, it improves the safety of the products, and also enhances the effectiveness thereof.

Thirdly, the sequence of the anti-EGFR single-chain antibody (scFv) is derived from cetuximab which has a glycosylation site (Asn88) modification, an important cause of clinical allergic reactions, in the variable region of the heavy chain. In the present disclosure, the variable region of the heavy chain of the antibody is subjected to a point mutation N88Q (SEQ ID NO. 12), which can remove the glycosylation site in the variable region, thereby reducing the immunogenicity of the CAR-T cell in human body and increasing the safety of clinical application thereof.

BRIEF DESCRIPTION OF THE DRAWINGS

FIG. 4B is a schematic diagram showing the structure of the chimeric antigen receptor (CAR);

DETAILED DESCRIPTION

In order to further illustrate the technical measures adopted by the present application and the effects thereof, the technical solutions of the present application is further described below with reference to the specific embodiments and accompanying drawings, but the present disclosure is not limited within the scope of the examples.

Example 1 Detection of the Levels of CXCL13 by ELISA

Figure 1:
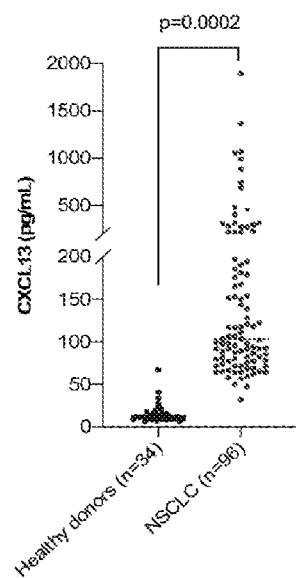
FIG. 1 shows the comparison of serum levels of CXCL13 in NSCLC patients and healthy donors.

As we know that the corresponding receptor to CXCL13 is CXCR5. We initially checked CXCL3 protein levels in NSCLC patient blood samples. Serum samples were obtained from 96 NSCLC patients and 34 healthy donors. The study was approved by the research ethics committees of all participating sites. The CXCL13 level in the blood serum was quantified by CXCL13 ELISA Kit from Origen, Inc according to the manufacturer's instructions. Compared to healthy control, CXCL13 levels in NSCLC patient serum increased about 3 fold (FIG. 1 and Table 1).

TABLE 1

The levels of CXCL13 in NSCLC patient blood serum (pg/mL)

|  | Healthy control (n = 34) | NSCLC patient (n = 96) |
|---|---|---|
| Median (95% CI) | 12.13 (9.13-15.24) | 103.50 (91.59-128.10) |
| Mean (±SD) | 15.65 ± 11.96 | 213.30 ± 297.7 |

Example 2 Detection of CXCL13 Expression by Immunohistochemistry (IHC)

Figure 2:
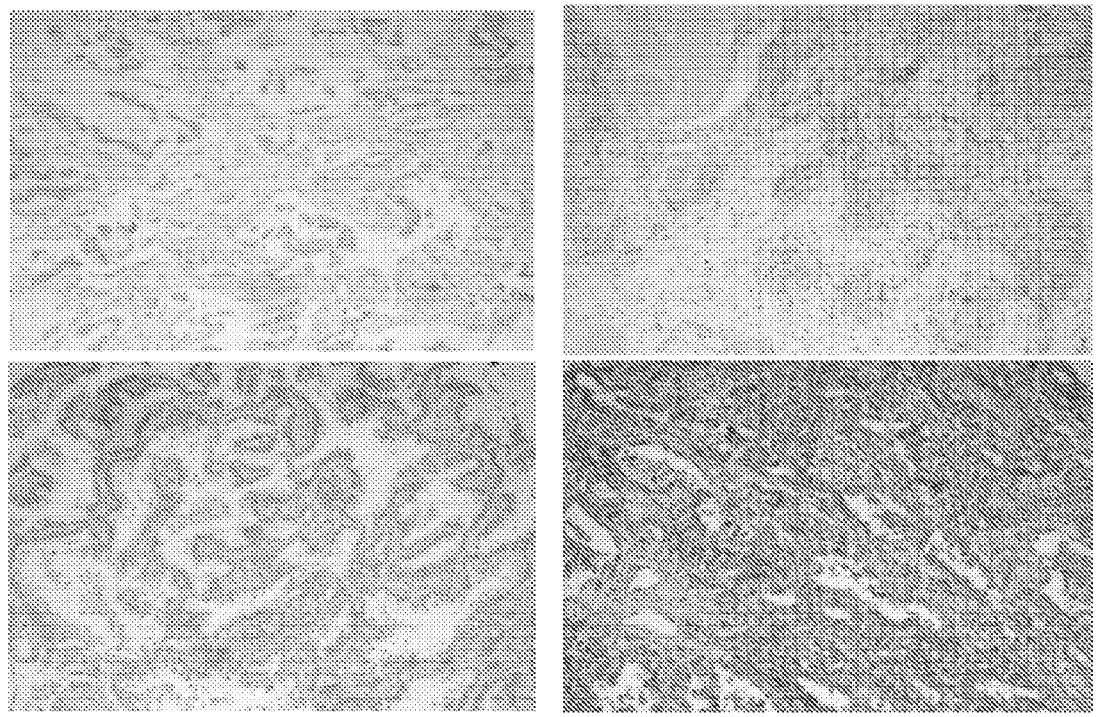
FIG. 2 shows representative pictures of CXCL13 expression in lung cancer by immunohistochemistry (IHC)

Furthermore, we checked CXCL13 expression in lung cancer tissues using tissue arrays. Two lung cancer tissue arrays LC20813b and NSC157 (US Biomax) were used in this study, each containing 192 and 150 of lung cancer cases, respectively. IHC staining suggested that about 70% of those samples were CXCL13 positive and 50% of them showed moderate to high levels of CXCL13 expression (FIG. 2 and Table 2), confirming the previous findings about CXCL13 expressions in lung cancer patients.

TABLE 2

Expression of CXCL13 in lung cancer tissue microarrays by immunohistochemistry (IHC).

| Expression | Intensity | LC20813b (n = 192) | Percentage (%) |
|---|---|---|---|
| Low expression | − | 58 | 30.5 |
|  | + | 53 | 27.9 |
| High expression | ++ | 48 | 25.3 |
|  | +++ | 31 | 16.3 |

| Expression | Intensity | NSC157 (n = 150) | Percentage (%) |
|---|---|---|---|
| Low expression | − | 46 | 30.7 |
|  | + | 34 | 22.7 |
| High expression | ++ | 35 | 23.3 |
|  | +++ | 35 | 23.3 |

Figure 3A:
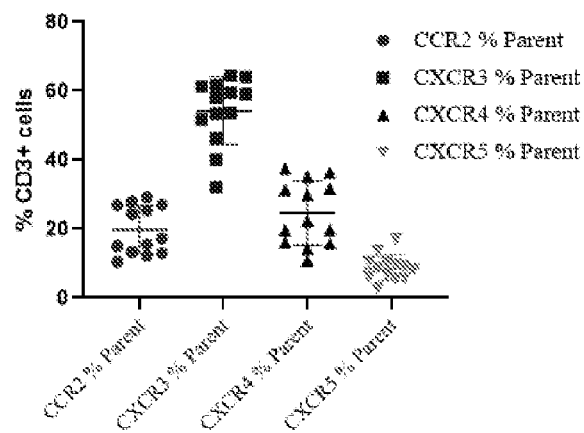
FIG. 3A shows the expression of chemokine receptors CCR2b, CXCR3, CXCR4 and CXCR5 on T cells in health donors (n=13)
Figure 3B:
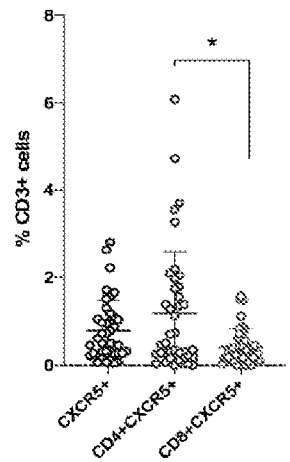
FIG. 3B shows the CXCR5 expression on CD4+ and CD8+ T cells.

Example 3 Detection of the Expression of Chemokine Receptors CCR2b, CXCR3, CXCR4 and CXCR5 on T Cells in Health Donors with Flow Cytometry We investigated whether normal T cells express CXCR5. We found that CXCR3 and CXCR4 are expressed in more than 20% of T cells. However, CXCR5 expressions are very low in normal T cells, less than 2% (FIG. 3A). We further confirmed that CXCR5 is expressed in about 1-2% of CD4 T cells, but not in CD8 T cells (FIG. 3B). This is consistent with that CXCR5 is constitutively expressed in follicular helper T cells ($T_H$). This CD4 T cell population usually comprises ~2% of all T cells and plays a critical role in mediating the selection and survival of B cells in germinal centers.

Example 4 CAR Design

Figure 4A:
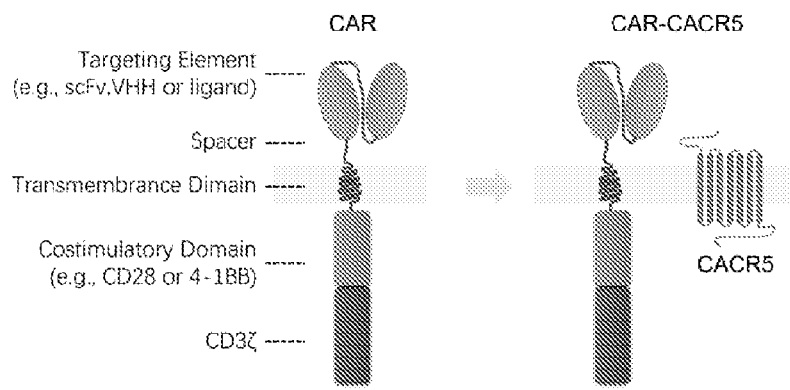
FIG. 4A shows the structure of the chimeric antigen receptor (CAR)

Chimeric antigen receptors (CARs) targeting 11 types of tumor antigens and CXCR5-fused chimeric antigen receptors (CXCR5-CARs) targeting 11 types of tumor antigens were constructed in this example. The schematic diagrams are shown in FIGS. 4A and 4B. The structure of CAR included a signal peptide sequence (leader), a targeting element (e.g., scFv, VHH or a ligand), a hinge domain (a spacer), a transmembrane domain, a costimulatory domain (e.g., CD28 or 4-1BB), and a CD3ξ signal conduction domain. For CXCR5-CAR, in addition to the CAR structure, it also included a CXCR5 sequence, which was connected by a self-cutting 2A linker.

The targets, antibodies, and indications of CAR-T were shown in Table. 3.

TABLE 3

Targets, antibodies, and indications of CAR-T

| Target | Source of scFv | Indications |
|---|---|---|
| CD19 | FMC63 | B-ALL; NHL; |
| CD20 | Rituximab | B-ALL; NHL; |
| BCMA | BCMB69(WO2017/031104 EN) | Multiple myeloma; MDS |
| CLL1 | 1075.7 | AML; |
| EGFR | Cetuximab | Lung cancer; Colon cancer; Head and neck cancer; |
| B7H3 | Enoblituzumab | Lung cancer; colon cancer; cervical cancer; Melanoma; Pancreatic cancer; |
| HER2 | Trastuzumab | Gastric cancer; Breast cancer; Ovarian cancer; |
| GD2 | 14G2a | Melanoma; Neuroblastoma; |
| GPC3 | 9F2(WO/2019/024933) | Liver cancer; |
| MUC1 | 5E5 | Pancreatic cancer; Breast cancer; |
| PSMA | huJ591 | Prostate cancer; |

Example 5 Construction of Lentiviral Vectors (1) The CARs and CXCR5-CARs were synthesized by whole gene synthesis. The CAR synthesized by whole gene synthesis and an empty vector were digested with EcoRI and BamHI in a water bath at 37° C. for 30 min. Then DNA electrophoresis was performed with a 1.5% agarose gel, and then purified and recovered with an agarose gel kit from Tiangen.

(2) Ligation of the pCDH-EF1-MCS vector with the CAR/CAR-CXCR5 gene fragment:

The ligation system is shown in Table 4:

TABLE 4

| Components | Volume (μL) |
|---|---|
| pCDH-EF1-MCS Vector | 2 (50 ng) |
| CAR/CAR-CXCR5 Gene | 10 (150 ng) |
| T4 DNA Ligation buffer | 2 |
| T4 DNA Ligase (NEB) | 1 |
| dd H$_2$O | 5 |
| Total | 20 |

The ligation was carried out at 22° C. for 1 h, then the product of which was directly used for transforming E. coli Stb13 competent cells. 200 μL of the transformed product was then plated on LB media with ampicillin, and the LB plate was inverted and cultured overnight in an incubator at 37° C. The next morning, 3 single clones were randomly selected for identification with colony PCR, and then positive clones were sent for sequencing.

The lentiviral vectors and contained CAR sequences were shown in Table. 5. The resultant CAR constructs were sequence verified and used for downstream applications.

TABLE 5

Construction and identification of lentiviral vectors

| Target | Lentiviral vector | CAR | SEQ ID No. |
|---|---|---|---|
| CD19 | pCDH-CD19-CAR | CD19-CAR | SEQ ID NO. 1 |
|  | pCDH-CD19-CXCR5 CAR | CD19-CXCR5 CAR | SEQ ID NO. 2 |
| CD20 | pCDH-CD20-CAR | CD20-CAR | SEQ ID NO. 3 |
|  | pCDH-CD20-CXCR5 CAR | CD20-CXCR5 CAR | SEQ ID NO. 4 |
| BCMA | pCDH-BCMA-CAR | BCMA-CAR | SEQ ID NO. 5 |
|  | pCDH-BCMA-CXCR5 CAR | BCMA-CXCR5 CAR | SEQ ID NO. 6 |
| CLL1 | pCDH-CLL1-CAR | CLL1-CAR | SEQ ID NO. 7 |
|  | pCDH-CLL1-CXCR5 CAR | CLL1-CXCR5 CAR | SEQ ID NO. 8 |
| EGFR | pCDH-EGFR-CAR | EGFR-CAR | SEQ ID NO. 9 |
|  | pCDH-EGFR-CXCR5 CAR | EGFR-CXCR5 CAR | SEQ ID NO. 10 |
| B7H3 | pCDH-B7H3-CAR | B7H3-CAR | SEQ ID NO. 11 |
|  | pCDH-B7H3-CXCR5 CAR | B7H3-CXCR5 CAR | SEQ ID NO. 12 |
| HER2 | pCDH-HER2-CAR | HER2-CAR | SEQ ID NO. 13 |
|  | pCDH-HER2-CXCR5 CAR | HER2-CXCR5 CAR | SEQ ID NO. 14 |
| GD2 | pCDH-GD2-CAR | GD2-CAR | SEQ ID NO. 15 |
|  | pCDH-GD2-CXCR5 CAR | GD2-CXCR5 CAR | SEQ ID NO. 16 |
| GPC3 | pCDH-GPC3-CAR | GPC3-CAR | SEQ ID NO. 17 |
|  | pCDH-GPC3-CXCR5 CAR | GPC3-CXCR5 CAR | SEQ ID NO. 18 |
| MUC1 | pCDH-MUC1-CAR | MUC1-CAR | SEQ ID NO. 19 |
|  | pCDH-MUC1-CXCR5 CAR | MUC1-CXCR5 CAR | SEQ ID NO. 20 |
| PSMA | pCDH-PSMA-CAR | PSMA-CAR | SEQ ID NO. 21 |
|  | pCDH-PSMA-CXCR5 CAR | PSMA-CXCR5 CAR | SEQ ID NO. 22 |

Example 6 Packaging and Titer Detection of Lentivirus

Lentiviral vector supernatant for the CAR or CXCR5-CAR was produced by transient transfection of adherent 293T cells (Takada) with the corresponding CAR plasmid and 3 packaging plasmids. The medium was exchanged 4 hours after transfection 4 h. After an additional 48 hours, the cell supernatant was pooled and filtered with a 0.451 m filter, followed by Benzonase treatment for 18 hours. Then, the harvest was passed through a Mustang Q ion-exchange capsule (Pall, Ann Arbor, Mich.). The Mustang Q membrane was washed using 50 mM Tris-HCl, pH 8.0 with 750 mM NaCl and then eluted in fractions using 50 mM Tris-HCL, pH 8.0 with 1.5 M NaCl and diluted with phosphate buffer pH 7.2. The elution was further concentrated approximately 10-fold by 300 KD TFF column. The final concentrate was formulated with HSA to 2%, filtered with a 0.22 um filter, aliquoted to 2 ml cryotubes, quick frozen on dry-ice, and stored at −80° C.

293T cells were plated on a 24-well plate at a density of 1E+5 cells/well 24 h in advance. 10 µl, 1 µl, 0.5 µl, 0.1 µl of lentivirus concentrate were added and incubated for 72 h. Then 200 µl of PBS solution containing FITC-Labeled Recombinant Protin L antibody at a ratio of 1:40 was added and incubated for 30 min in the dark. The positive ratio was detected by flow cytometry, and the infectious titer was calculated. See Table. 6.

TABLE 6

Packaging and titer of lentivirus

| Lentivirus | CAR | Titer (TU) | Storage |
|---|---|---|---|
| LV-CD19-CAR | CD19-CAR | $2.67 \times 10^7$/mL | −80° C. |
| LV-CD19-CXCR5 CAR | CD19-CXCR5 CAR | $2.55 \times 10^7$/mL | −80° C. |
| LV-CD20-CAR | CD20-CAR | $3.54 \times 10^7$/mL | −80° C. |
| LV-CD20-CXCR5 CAR | CD20-CXCR5 CAR | $3.46 \times 10^7$/mL | −80° C. |
| LV-BCMA-CAR | BCMA-CAR | $3.87 \times 10^7$/mL | −80° C. |
| LV-BCMA-CXCR5 CAR | BCMA-CXCR5 CAR | $3.57 \times 10^7$/mL | −80° C. |
| LV-CLL1-CAR | CLL1-CAR | $2.55 \times 10^7$/mL | −80° C. |
| LV-CLL1-CXCR5 CAR | CLL1-CXCR5 CAR | $3.65 \times 10^7$/mL | −80° C. |
| LV-EGFR-CAR | EGFR-CAR | $3.24 \times 10^7$/mL | −80° C. |
| LV-EGFR-CXCR5 CAR | EGFR-CXCR5 CAR | $3.68 \times 10^7$/mL | −80° C. |
| LV-B7H3-CAR | B7H3-CAR | $2.88 \times 10^7$/mL | −80° C. |
| LV-B7H3-CXCR5 CAR | B7H3-CXCR5 CAR | $2.34 \times 10^7$/mL | −80° C. |
| LV-HER2-CAR | HER2-CAR | $2.97 \times 10^7$/mL | −80° C. |
| LV-HER2-CXCR5 CAR | HER2-CXCR5 CAR | $2.66 \times 10^7$/mL | −80° C. |
| LV-GD2-CAR | GD2-CAR | $3.54 \times 10^7$/mL | −80° C. |
| LV-GD2-CXCR5 CAR | GD2-CXCR5 CAR | $4.15 \times 10^7$/mL | −80° C. |
| LV-GPC3-CAR | GPC3-CAR | $4.12 \times 10^7$/mL | −80° C. |
| LV-GPC3-CXCR5 CAR | GPC3-CXCR5 CAR | $3.45 \times 10^7$/mL | −80° C. |
| LV-MUC1-CAR | MUC1-CAR | $3.47 \times 10^7$/mL | −80° C. |
| LV-MUC1-CXCR5 CAR | MUC1-CXCR5 CAR | $3.13 \times 10^7$/mL | −80° C. |
| LV-PSMA-CAR | PSMA-CAR | $2.78 \times 10^7$/mL | −80° C. |
| LV-PSMA-CXCR5 CAR | PSMA-CXCR5 CAR | $3.47 \times 10^7$/mL | −80° C. |

Example 7 Detection of CAR and CXCR5 Expression with Flow Cytometry

CAR expression was detected using 200 μl of PBS solution containing FITC-Labeled Recombinant Protin L antibody at a ratio of 1:40 and CXCR5 expression was detected using anti-CXCR5 antibody (1:200).

TABLE 7

Expression of CAR and CXCR5 on CAR-T cells

| CAR-T cells | CAR+ (%) | CXCR5+ (%) | CAR+CXCR5+ (%) |
|---|---|---|---|
| CD19-CAR | 34.2 | 3.5 | 1.5 |
| CD19-CXCR5 CAR | 37.7 | 42.5 | 35.1 |
| CD20-CAR | 57.6 | 2.1 | 22.4 |
| CD20-CXCR5 CAR | 59.5 | 45.2 | 43.5 |
| BCMA-CAR | 68.5 | 1.7 | 1.0 |
| BCMA-CXCR5 CAR | 65.3 | 67.2 | 59.1 |
| CLL1-CAR | 49.8 | 1.8 | 1.1 |
| CLL1-CXCR5 CAR | 40.2 | 45.2 | 45.1 |
| EGFR-CAR | 56.5 | 2.2 | 1.3 |
| EGFR-CXCR5 CAR | 49.9 | 45.2 | 43.8 |
| B7H3-CAR | 70.6 | 1.3 | 0.8 |
| B7H3-CXCR5 CAR | 65.6 | 68.4 | 64.3 |
| HER2-CAR | 45.9 | 0.7 | 0.4 |
| HER2-CXCR5 CAR | 44.2 | 45.6 | 41.2 |
| GD2-CAR | 37.2 | 2.7 | 1.1 |
| GD2-CXCR5 CAR | 38.9 | 35.4 | 31.2 |
| GPC3-CAR | 55.4 | 1.4 | 0.9 |
| GPC3-CXCR5 CAR | 49.8 | 48.5 | 44.5 |
| MUC1-CAR | 44.8 | 1.7 | 0.7 |
| MUC1-CXCR5 CAR | 49.1 | 50.2 | 42.7 |
| PSMA-CAR | 56.3 | 1.9 | 0.2 |
| PSMA-CXCR5 CAR | 45.1 | 44.3 | 43.1 |

Example 8 In Vitro Cell Migration Assay (Transwell)

Transwell cell migration assay was used to explore the effect of chemokine CXCR5 on the chemotactic ability of CAR-T, which comprised the following specific steps:

1) To the lower chamber of a Transwell insert having a pore size of 5 μm was added serum-free media containing 0, 1, or 5 g/mL of recombinant Human CXCL13 (purchased from Beijing Yiqiao Shenzhou Biotechnology Co., Ltd. Cat: 10621-HNAE) respectively; wherein T cell media was T cell amplification serum-free media (TAKARA company; Cat: GT-T551H3)

Figure 5:
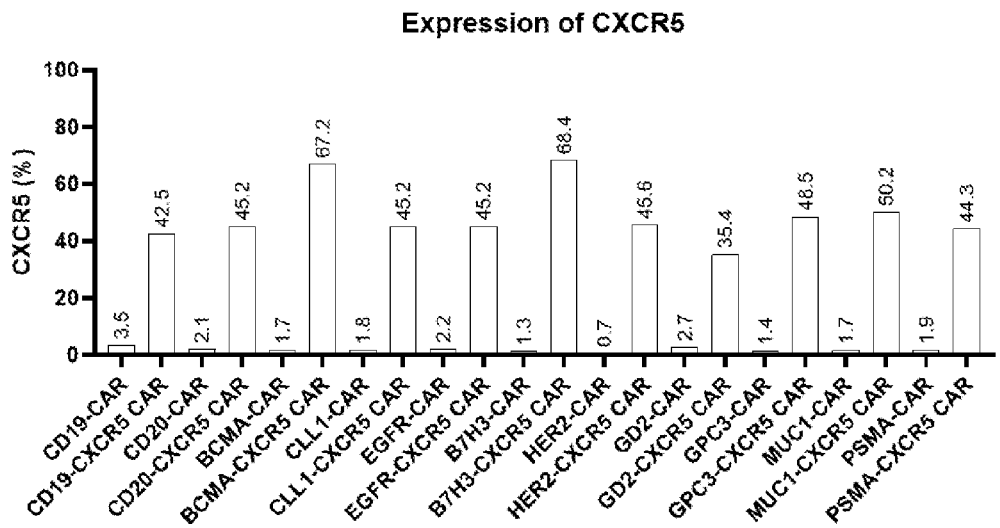
FIG. 5 shows the expression of CXCR5 on CAR-T cells.
Figure 6:
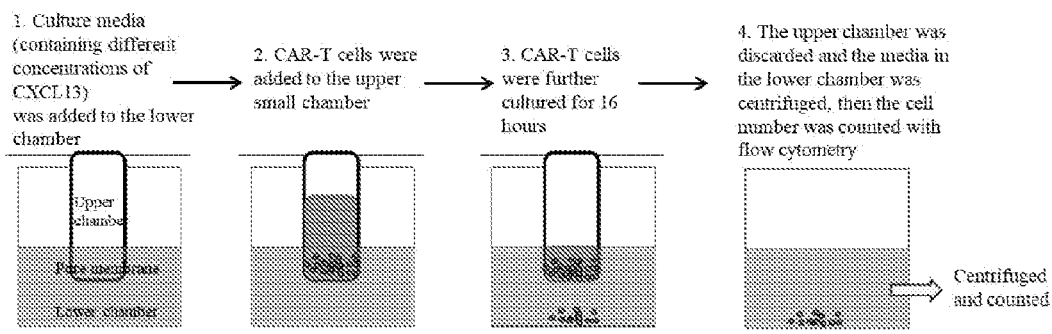
FIG. 6 is a schematic diagram showing the process of the migration experiment.
Figure 7:
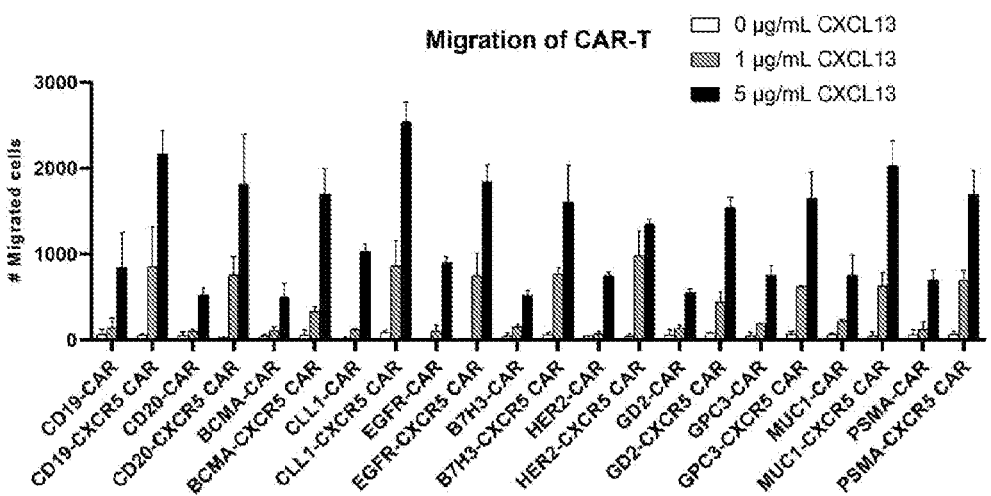
FIG. 7 is a diagram showing the results of the migration experiment (16 h)
Figure 8:
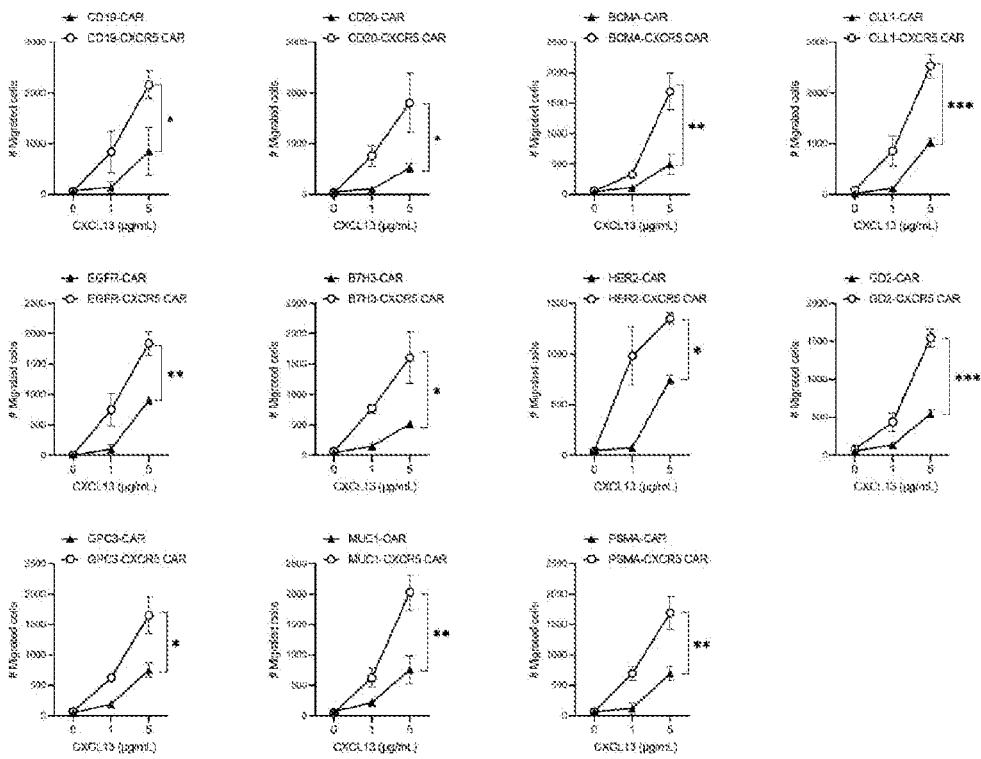
FIG. 8 shows the enhanced migration of CXCR5+ CAR-T cells.

2) EGFR-CAR T cells and EGFR-CXCR5-CAR T cells were collected from step 2, centrifuged, and counted;

3) 1×10$^5$ of CAR-T cells were re-suspended in 200 μL of serum-free media, mixed and added to the upper chamber;

4) further cultured for 16 h, then the upper chamber was discarded and the media and cells in the lower chamber was pipetted;

5) after centrifugation, the cell pellet was re-suspended in PBS, and analyzed and counted with flow cytometry. The schematic diagram of the assay is shown in FIG. 5, and the results are shown in FIG. 6.

The results show that compared to CAR T groups, more cells in the groups of 11 types of CAR T cells expressing CXCR5 migrated into the lower chamber. This phenomenon was observed in both groups containing 1 and 5 μg/mL of recombinant human CXCL13, suggesting that CXCR5 expression can effectively enhance the chemotactic migration ability of CAR-T cells. This phenomenon was universal. CXCR5 can be used in a variety of CAR-T cells to improve their migration capabilities.

Example 9 Killing Effect of CAR-T Cells on Target Cells

Figure 9:
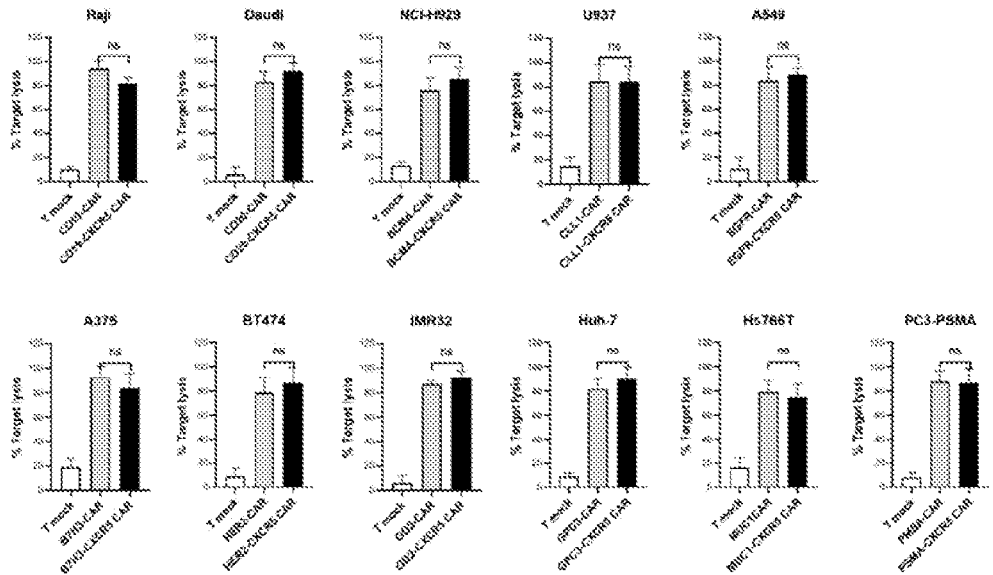
FIG. 9 shows the target lysis by CAR-T cells.

Killing assays were performed by co-culturing 50,000 CAR+ T cells with 50,000 CellTrace Far Red-labeled tumor cells in complete media in a 96 well plate with SYTOX Green as an indicator of dead cells. Briefly, CellTrace Far Red-stained tumor cells (target cells) were seeded into 96-wells at a density of 50000 cells/well. Subsequently, non-transduced T cells (T mock), CAR, or CAR-CXCR5 T cells (effector cells) were added to each well to ensure an effector:target cell (E:T) ratio of 1:1. Percentage of tumor cells killing was calculated by dividing the CellTrace Far Red and SYTOX Green double positive tumor cells with total number of CellTrace Far Red positive tumor cells. As shown in FIG. 9, CAR and CAR-CXCR5 T cells targeting different antigens efficiently lysed their respective target cells, but not the non-transduced T cells (T mock).

Example 10 Cytotoxicity and Cytokine Secretion of EGFR-CXCR5 CAR-T

Figure 10:
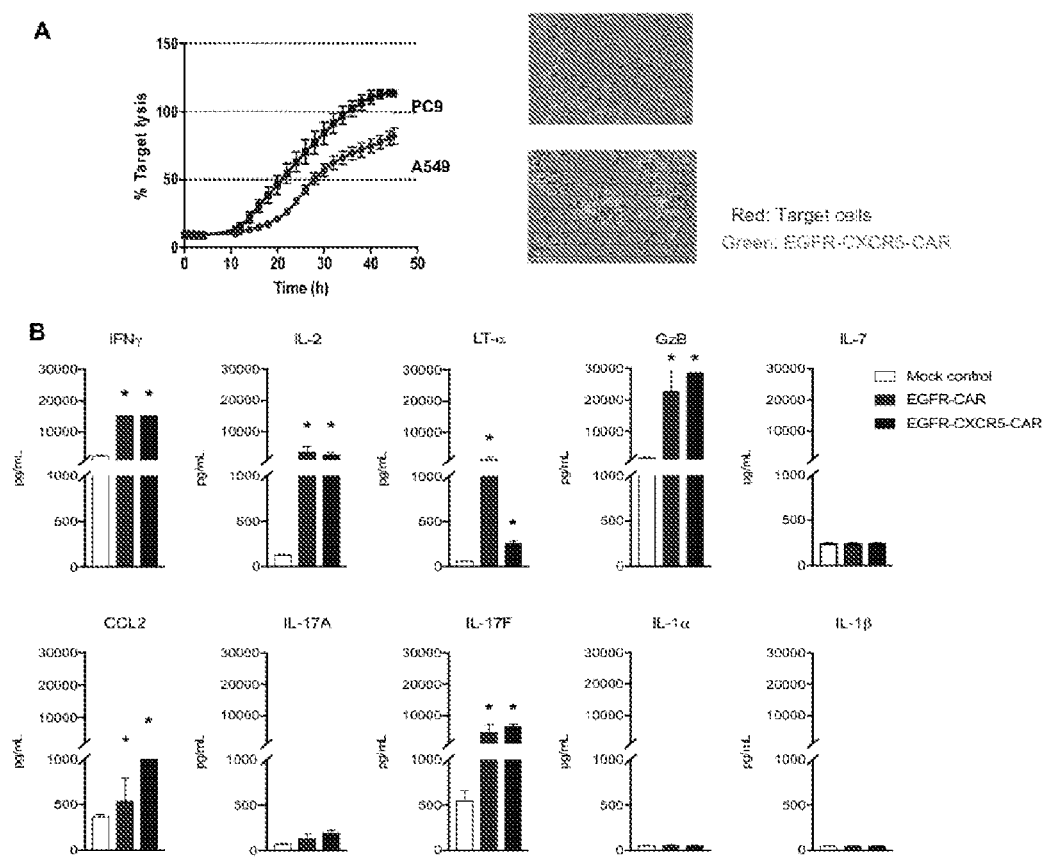
FIG. 10 shows cytotoxicity and cytokine secretion of EGFR-CXCR5 CAR-T.

Images were acquired every 2 hours using an Incucyte (Sartorius). Percentage of tumor cells killing was calculated by dividing the CellTrace Far Red and SYTOX Green double positive tumor cells with total number of CellTrace Far Red positive tumor cells at every time point by the same measurement at the first time point. The results demonstrated that EGFR-CXCR5-CAR is efficient to lysis almost 100% of EGFR positive cells (FIG. 10A).

Cytokine levels in the cell culture supernatant (IFNγ, IL-2, granzyme B, LT-α, IL-7. IL-17A, IL-17F, IL-1α, IL-β) and mice serum (IFNγ, granzyme B, 11-2, IL-6, IL-7, IL-10) were quantified using a cytometric bead array (CBA; Becton Dickinson Biosciences) according to the manufacturer's instructions, with the modification that volumes of all reagents and samples were 10% of those in the original protocol. Data were collected using a Beckman Coulter CytoFlex flow cytometer (Beckman Coulter) and analyzed with FlowJo software (Tree-Star). The concentration of cytokine was calculated by standard curve regression. Human CXCL13 from human donor serums, human IFNγ and IL-2 from cell culture supernatant were measured by enzyme-linked immunosorbent assay (ELISA) development kit (4A Biotech, Beijing) and used according to the manufacturer's instructions. Cytokine concentrations were calculated by standard curve regression. We observed high levels of IFNγ, IL-2 and Granzyme B. There were no significant differences between cytokines released by EGFR-CAR and EGFR-CXCR5-CAR, suggesting that the ectopic expression of CXCR5 does not affect T cell cytotoxicity function (FIG. 10B).

Example 11 Isotope Labeling and Biodistribution of CAR-T Cells In Vivo

Figure 11:
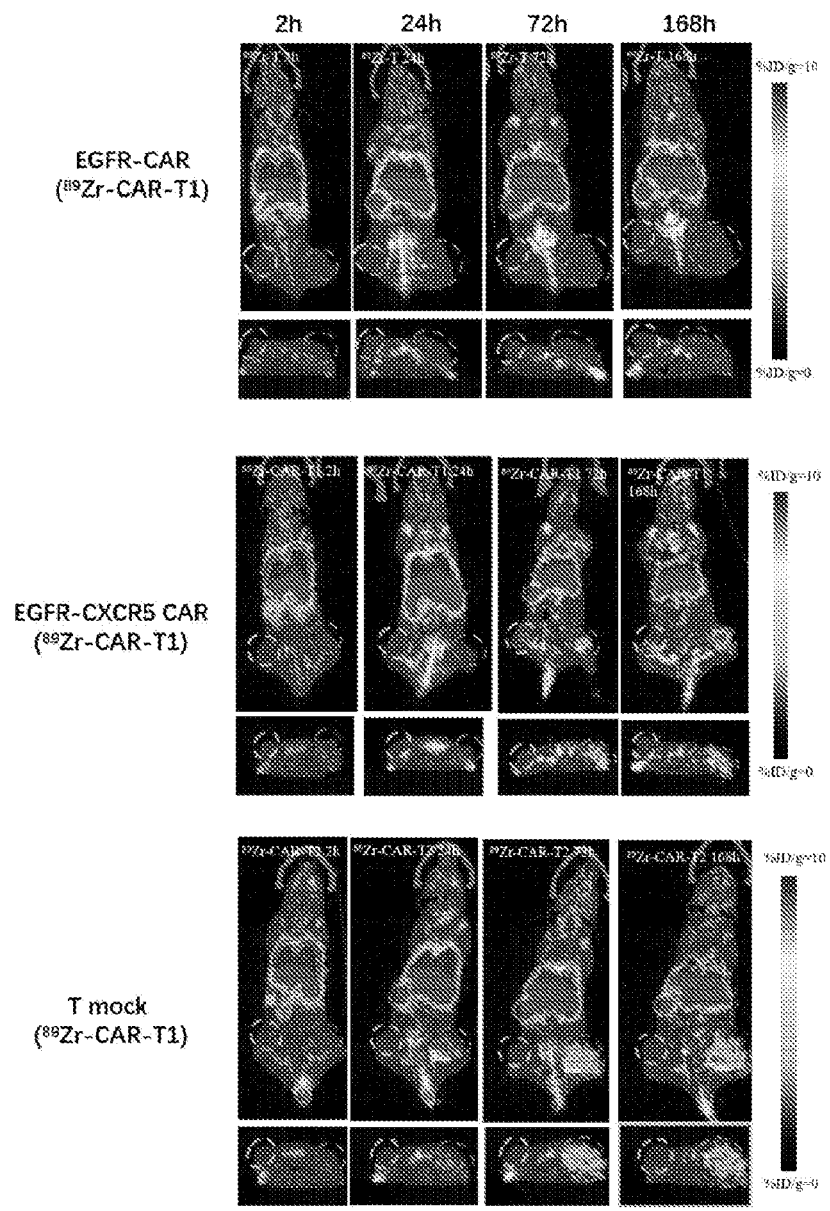
FIG. 11 shows animal scanning map for tracking CAR-T distribution by a PET/CT Scan.

To confirm that the addition of CXCR5 facilitates T cell migration to CXCL13 positive tumors in vivo, we labeled CAR-T cells with radio-isotope. To generate CXCL13 positive tumors, we stably transfected CXCL13 in EGFR positive cancer cell line A549 (A549-CXCL13). The mice were inoculated with A549 cells at the left side, and A519-CXCL13 at the right to differentiate CXCL13 negative and positive tumors. Then $^{89}$Zr was used to label fresh CAR-T cells. The labeling efficiency reached more than 90%, and the cell viability was also more than 90% after labeling. $^{89}$Zr-labeled CAR-T cells were injected into the mice from the tail vein, and T cell bio-distribution was checked at 2 h, 24 h, 72 h and 168 h post-injection. In general, T cells initially accumulated in lung, and then spread to spleen in mice. As for the tumor sites, single EGFR-CAR cells moved to both the left and right tumor sites, though slightly more at the right site possibly due to the 1-2% CXCR5 expression in the original native T cells. However, the EGFR-CXCR5-CAR showed a much higher number of cell migration to the CXCL13 positive side. As a control, the mock T cells do not migrate to the left or right tumor site (FIG. 11) as expected.

Figure 12:
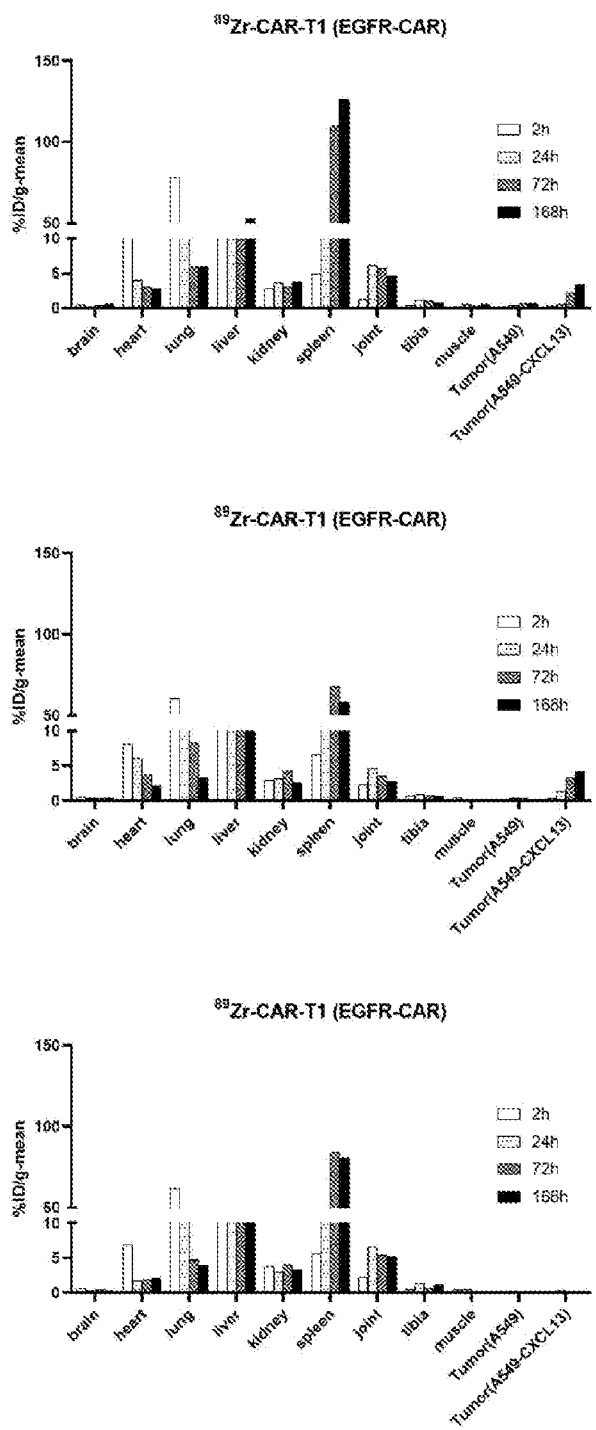
FIG. 12 shows histograms of % ID/g-mean in various tissues of M-NSG mice.

The distribution of radioactive substance is mainly in spleen, liver and lung, followed by heart and kidney, and the distribution of radioactive substance in brain and muscle is very low. (FIG. 12)

Figure 13:
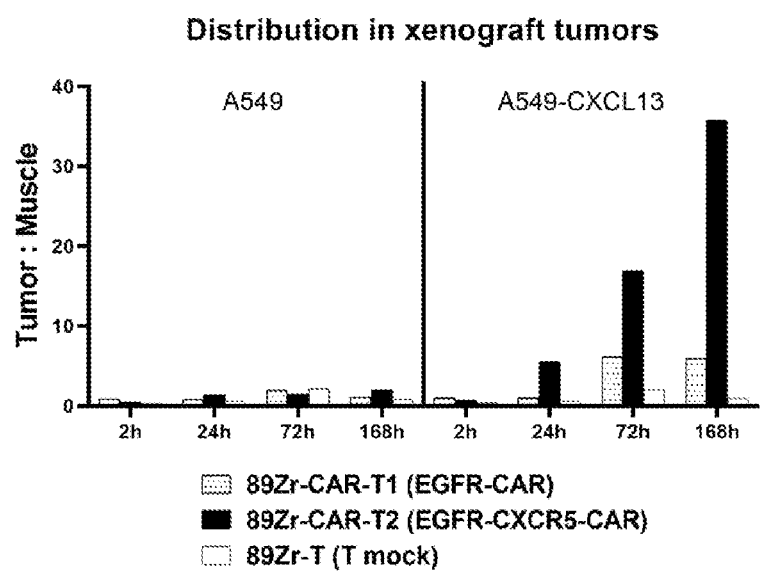
FIG. 13 shows the histogram of the ratio of tumor uptake value (% ID/g-mean) to muscle.

Quantification of the radio-isotope signal in vivo confirmed that EGFR-CXCR5-CAR cells at CXCL13 positive site showed the highest intensity, about 3-fold higher at 72 h, and 7-fold higher at 168 h compared with EGFR-CAR (FIG. 13).

Figure 14:
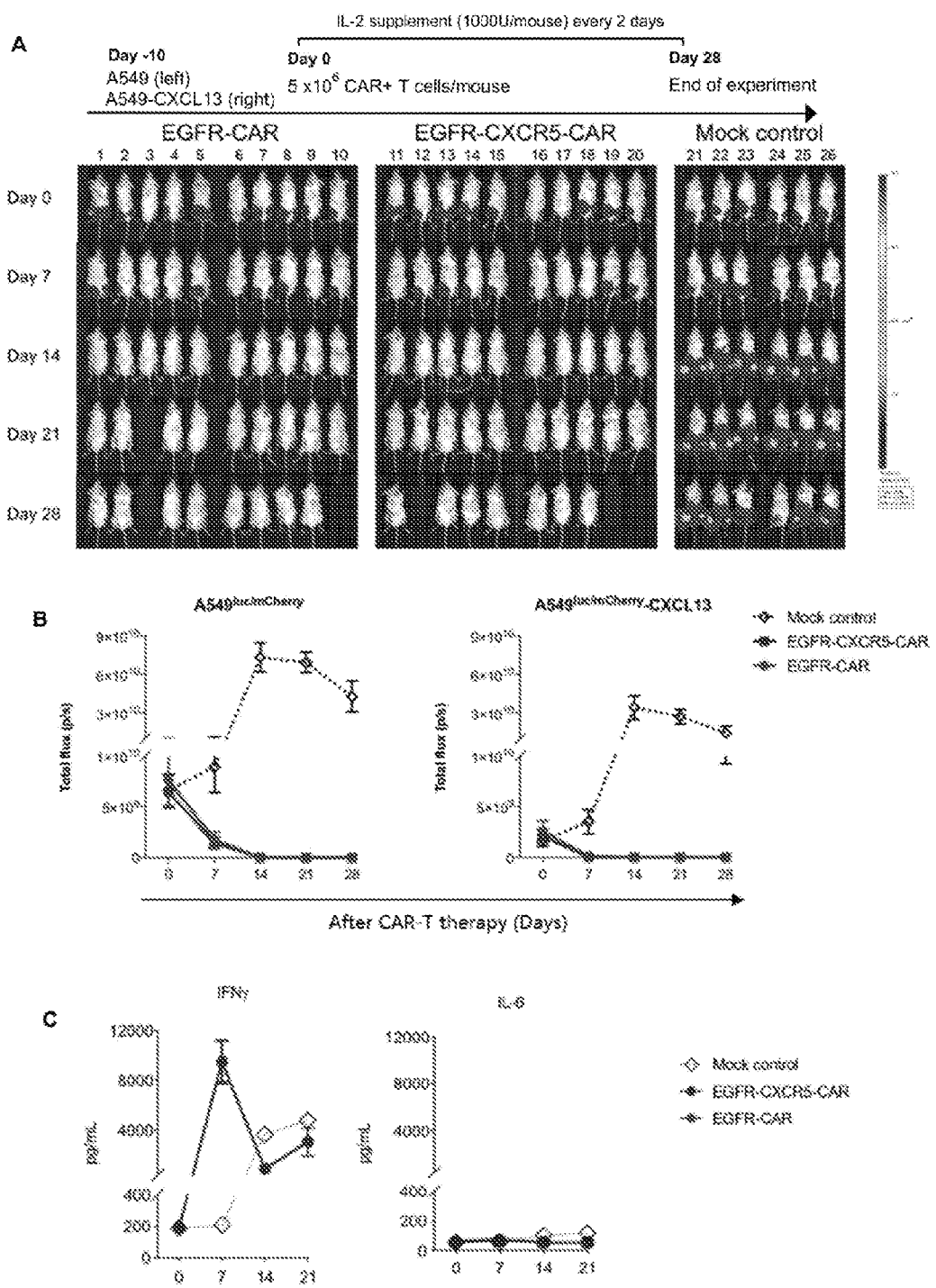
FIG. 14 shows the in vivo A549-luc and A549-CXCL13-luc tumor growth in tumor-bearing mice treated with CAR-T; (A) In vivo imaging of lung cancer in mice model; (B) Tumor size of each group; (C) IFN-γ and IL-6 levels in serum of mice after CAR-T therapy.

Example 12: Systemically Administered EGFR-CXCR-CAR T Cells can Clear CXCL13 Positive Lung Cancer Xenografts In Vivo We next tested the ability of each type of activated T cells to exert anti-tumor activity in vivo. In this experiment, the tumor cell lines A549 and A549-CXCL3 were labeled with Luciferase fluorescence and inoculated at the mice left and right sides, the same as above. After 10 days, when the tumors were established, CAR-T cells were injected into the mice from the tail vein, followed by IL-2 injection every 2 days. Preferential clearances of A549-CXCL13 tumors were observed for both EGFR-CAR and EGFR-CXCR5-CAR. It was possibly because the initial tumor size for A549-CXL13 was also smaller, although the same number of tumor cells were inoculated. At day 14, all the tumors were cleared compared to T mock control (FIG. 14A-B). The mice blood samples were collected at days 0, 7 14 and 21. High IFNγ levels in the blood serum were observed at day 7, and there was no difference between single EGFR-CAR and EGFR-CXCR5-CAR, which was consistent with in vitro data that CXCR5 did not affect T cell killing capability (FIG. 14C).

In summary, the present disclosure provides use of chemokine receptor CXCR5, wherein CAR-T cells with enhanced chemotaxis are obtained by modifying chimeric antigen receptor T cells (CAR-T cells) utilizing the chemotactic signal between CXCR5 and its ligand CXCL13. The chemokine receptor CXCR5 can guide CAR-T cells to migrate to tumors. It has an excellent ability to enhance the chemotaxis of CAR-T cells, can specifically clear tumor cells, and effectively solve the problem of poor efficacy of the existing CAR-T therapy for solid tumors, thereby exhibiting broad application prospects and great market value.

The applicant states that detailed methods of the present disclosure are demonstrated in the present disclosure through the above examples, however, the present disclosure is not limited to the above detailed methods, and does not mean that the present disclosure must rely on the above detailed methods to implement. It should be apparent to those skilled in the art that, for any improvement of the present disclosure, the equivalent replacement of the raw materials of the present disclosure, the addition of auxiliary components, and the selection of specific modes, etc., will all fall within the protection scope and the disclosure scope of the present disclosure.

The invention claimed is:

1. A chimeric antigen receptor targeting a tumor antigen, comprising an antigen receptor portion and a chemokine receptor CXCR5 portion.

2. A method for preparing the chimeric antigen receptor of claim 1 comprising modifying an antigen receptor with a chemokine receptor CXCR5.

3. The method according to claim 2, wherein the chimeric antigen receptor targets a tumor antigen.

4. The chimeric antigen receptor according to claim 1, wherein the tumor antigen is any one or a combination of at least two of the group consisting of CD19, CD20, BCMA, CLL1, EGFR, B7H3, HER2, GD2, GPC3, MUC1 and PSMA.

5. The chimeric antigen receptor according to claim 1, wherein the chimeric antigen receptor has the amino acid sequence as shown in any one of SEQ ID NOs. 2, 4, 6, 8, 10, 12, 14, 16, 18, 20 or 22.

6. A lentivirus obtained by packaging a plasmid comprising the chimeric antigen receptor according to claim 1 with a helper plasmid.

7. A pharmaceutical composition comprising the chimeric antigen receptor according to claim 1.

8. The pharmaceutical composition according to claim 7, wherein the pharmaceutical composition further comprises any one or a combination of at least two of the group consisting of a pharmaceutically acceptable carrier, a diluent and an excipient.

9. A method for treating a tumor comprising administrating a therapeutically effective amount of the pharmaceutical composition according to claim 7 to a patient in need thereof.

10. The method according to claim 9, wherein the tumor comprises any one or a combination of at least two of the group consisting of gastric cancer, liver cancer, lung cancer, esophageal cancer, cervical cancer, breast cancer, colon cancer, rectal cancer, nasopharyngeal cancer, ovarian cancer, kidney cancer, bladder cancer, thyroid cancer, skin cancer, glioma, neuroblastoma, melanoma and lymphoma.

11. The chimeric antigen receptor according to claim 1, wherein the antigen receptor portion is linked to the chemokine receptor CXCR5 portion via a self-cutting 2A linker.

12. The pharmaceutical composition according to claim 7, wherein the chimeric antigen receptor has the amino acid sequence as shown in any one of SEQ ID NOs. 2, 4, 6, 8, 10, 12, 14, 16, 18, 20 or 22.

13. The method according to claim 9, wherein the chimeric antigen receptor has the amino acid sequence as shown in any one of SEQ ID NOs. 2, 4, 6, 8, 10, 12, 14, 16, 18, 20 or 22.

* * * * *